(12) United States Patent
Kazerooni et al.

(10) Patent No.: US 9,327,025 B2
(45) Date of Patent: May 3, 2016

(54) ENRICHED 10-BORON COMPOSITION FOR CANCER THERAPY AND A METHOD OF SYNTHESIZING THE SAME

(71) Applicants: Hanif Kazerooni, Tehran (IR); Bahram Nasernejad, Tehran (IR); Abbas Abdolmalaki, Tehran (IR); Akbar Zare, Tehran (IR)

(72) Inventors: Hanif Kazerooni, Tehran (IR); Bahram Nasernejad, Tehran (IR); Abbas Abdolmalaki, Tehran (IR); Akbar Zare, Tehran (IR)

( * ) Notice: Subject to any disclaimer, the term of this patent is extended or adjusted under 35 U.S.C. 154(b) by 610 days.

(21) Appl. No.: 13/726,500

(22) Filed: Dec. 24, 2012

(65) Prior Publication Data

US 2014/0128658 A1   May 8, 2014

(51) Int. Cl.
*A61K 41/00* (2006.01)
*A61N 5/10* (2006.01)

(52) U.S. Cl.
CPC .............. *A61K 41/0095* (2013.01); *A61N 5/10* (2013.01); *A61N 2005/109* (2013.01)

(58) Field of Classification Search
None
See application file for complete search history.

(56) References Cited

U.S. PATENT DOCUMENTS

| | | | | |
|---|---|---|---|---|
| 5,962,049 | A * | 10/1999 | Miljkovic | A23G 1/325 426/658 |
| 6,169,076 | B1 * | 1/2001 | Shull | C07B 59/005 514/23 |
| 2008/0050309 | A1 * | 2/2008 | Witczak | A61K 41/009 424/1.11 |

* cited by examiner

*Primary Examiner* — Michael G Hartley
*Assistant Examiner* — Jennifer Lamberski
(74) *Attorney, Agent, or Firm* — Barry Choobin; Patent 360

(57) ABSTRACT

The embodiments herein provide a method of synthesizing a novel enriched 10-boron drug for treatment of cancer by Boron Neutron Capture Therapy (BNCT) method. In BNCT, drug containing enriched 10-Boron has the important role in final treatment efficiency. The composition is Enriched 10-Boron Calcium Fructo Borate ($E^{10}BCFB$). The Calcium Fructo-Borate is found in some vegetables. $E^{10}BCFB$ is in fact an artificial Calcium Fructo-Borate which is synthesized chemically with enriched 10-Boron. $E^{10}BCFB$ becomes an important competitor drug in the fight against some cancerous cells. The composition is applied orally and parenterally.

9 Claims, 32 Drawing Sheets

ENRICHED 10-BORON COMPOSITION FOR CANCER THERAPY AND A METHOD OF SYNTHESIZING THE SAME

CROSS-REFERENCE TO RELATED APPLICATION

This application claims the priority under 35 USC 35 119 (e) of U.S. Provisional Application Ser. No. 61/712,710 filed Oct. 11, 2012 which included by reference herein.

BACKGROUND

1. Technical Field

The embodiments herein generally relate to a cancer treatment and particularly to a neutron therapy used for the treatment of cancer. The embodiments herein more particularly relate to a Boron Neutron Capture Therapy (BNCT) for the treatment of cancer and a method of synthesizing a composition for treatment of cancer based on Boron neutron capture therapy.

2. Description of the Related Art

The Neutron therapy relates to the treatment of cancer by capturing neutrons using the neutron absorbent compositions with a large neutron capture cross section. The neutron therapy is indeed a type of radiotherapy and chemotherapy methods for treating the tumors. The neutron therapy has indeed taken into account both the aspects of chemotherapy and radiotherapy. The Boron Neutron Capture Therapy (BNCT) of cancer with sustainable $^{10}$B isotope is one of the conventional methods in this field.

The BNCT depends on an interaction of the slow neutrons with enriched 10-Boron to produce the alpha particles and lithium nuclei without producing any other types of ionizing radiations. The patients are first given an intravenous injection of an enriched 10-Boron tagged chemical that preferentially binds to the tumor cells. In the clinical trials performed so far, the neutrons are created in a nuclear reactor but the particle accelerators may also be used to make the protons to collide with the targets made of Lithium or Beryllium. The neutrons pass through a moderator which shapes the neutron energy spectrum suitable for the BNCT treatment. While passing through the tissues of the patient, the neutrons are slowed by the collisions and become low energy thermal neutrons. The thermal neutrons undergo a reaction with the 10-Boron nuclei to form a compound nucleus called excited 11-Boron. The excited 11-Boron then promptly disintegrates into 7-Lithium and an alpha particle. Both the alpha particle and the Lithium ion produce closely spaced ionizations in the immediate vicinity of a reaction with a range of approximately 5-9 micrometers or roughly the thickness of one cell diameter. This technique is advantageous since the radiation damage occurs over a short range and hence the normal tissues can be spared.

FIG. 1 shows an overall schematic view of the process of the entrance of the drug and the process of Boron Neutron Capture Therapy (BNCT) used in a prior art. With respect to FIG. 1, in the method of BNCT, the drugs or compositions are generated using sustainable $^{10}$B isotope. They are then delivered to the tumor site. As the concentration of $^{10}$B reaches 20 mcg $^{10}$B/g to 35 mcg $^{10}$B/g, then the tumor can be bombarded from outside using the thermal and epithermal neutrons depending on the type and location of the tumor so that the thermal and epithermal neutrons will lead to a nuclear reaction in micro scale dimensions of the cell containing composition. This reaction generates a large amount of energy which is capable of removing the cancerous cells.

The thermal neutron is a kind of low-energy neutrons which can be produced using a reactor or an accelerator or by reducing the energy of fast neutrons generated from them through an application of proper design. This neutron bombardment generates compositions containing $^{10}$B, alpha particles having high linear heat transfer energy (LET) comprised of $^4$He and $^7$Li. The nuclear reactions occurring in the process of BNCT are shown as following:

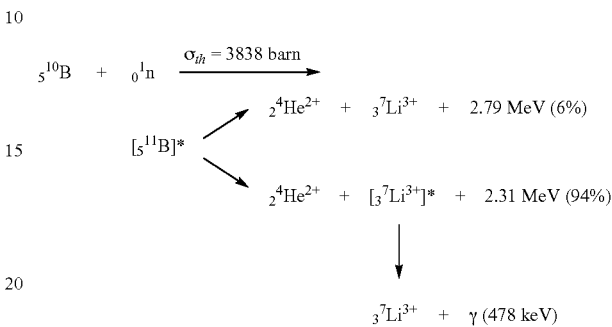

In order to make the BNCT method to be successful, a sufficient amount of $^{10}$B should be conveyed to the tumor location selectively for receiving a sufficient amount of thermal neutrons. Due to the fact that the particles containing high-LET are only the pathways for energy transfer in the tissues, the destructive effects of these particles is therefore restricted to the cells containing $^{10}$B. As the BNCT method is more biological in comparison to the other physical treatments that use radiation, it may potentially destruct the tumor cells that are scattered in the main and healthy tissues. It is evident that the field of studies of the existing technologies towards the development of BNCT is divided into three general categories.

FIG. 2 shows a schematic block diagram indicating the components required for delivering a Boron Neutron Capture Therapy (BNCT) according to a prior art. With respect to FIG. 2, the BNCT method uses three components for providing a treatment. The first one is the drugs containing enriched 10-Boron isotope. The drug should contain sufficient amount of 10-Boron isotope. The second one is 10-boron delivery agent should have no or minimal systematic toxicity with rapid clearance from blood and normal tissues. The third one is a transfer of sufficient amount of the drug to the cancer cells in a way so that the tumor tends to absorb the targeted chemical compositions containing $^{10}$B isotope. Some other points are to be considered are the concentration ratios of drug containing enriched 10-Boron isotope into the tumor to blood and the tumor to healthy tissues (greater than 3-4:1). The fourth one is persistence of the drug containing 10-Boron isotope in the tumor for a sufficient period of time to carry out BNCT. The fifth one is a sufficient number of $^{10}$B atoms (approximately $10^9$ atoms/cell) must be delivered selectively to the tumor (approximately 20 mcg $^{10}$B/g to 35 mcg $^{10}$B/g). The sixth one is a suitable source of thermal or epithermal neutron.

The $^{10}$B will be fissioned in or near the cancerous tumor after capturing the neutrons where the high-energy and heavy pieces resulted from the Boron fission will damage only their neighboring cells (due to dissipation of energy in low range because of the large mass of fissioned pieces) which are essentially cancerous cells (because of the absorption of targeted 10-Boron in the cancerous tissue) and as a result, the healthy tissues will get damaged minimally.

For a treatment with BNCT, the $^{10}$B isotope should be made available. The Boron compositions found in nature contain 80.1 (7)% of $^{11}$B and 19.9 (7)% of $^{10}$B. Hence the percentage of $^{10}$B has to be increased for synthesizing the active compositions in BCNT. This process of increasing $^{10}$B is called enrichment process. This kind of enriched Boron is commercially available and the different methods for separation of the isotopes from each other are also available [Annals of Nuclear Energy, 37, (2010) 1-4].

The different types of radiations are used and delivered to the cells. The different doses of radiation which are delivered to both the healthy and cancerous cells in the process of BNCT are of three types of directly ionizing radiations [Clinical Cancer Research 2005, 11(11) Jun. 1, 2005] with mutually different LET properties. These are (a) gamma rays with low LET energy which are temporarily resulted from the conversion of thermal neutrons through the hydrogen atoms of a healthy tissue [$^1$H (n, γ)$^2$H], (b) the protons containing high-energy LET that are produced through a rapid neutron scattering and through the conversion of thermal neutrons by the nitrogen atoms [$^{14}$N (n, p) $^{14}$C] and (c) the high LET heavy particles and $^7$Li ions that are shot as the outcome of the conversion of the thermal neutron and fission reactions with [$^{10}$B (n, α) $^7$Li]$^{10}$B.

The higher density of ionization along the axes of the particles having high linear energy leads to an increase of biological property in comparison to a similar physical dose from a LET radiation. This process is usually called as Relative Biological Effectiveness (RBE) which is the ratio of an absorbed dose of a reference radiation source (like X-ray) to the category of test radiations that generate the same biological effectiveness. Due to the fact that there are both tumor tissues and healthy peripheral tissues in the radiation field, there will be an inevitable underlying non-specific dose which comprises the high and low LET radiations (event ideal neutron beams). However, the higher overall doses will be absorbed through high densities of $^{10}$B in tumor comparing to the adjacent normal tissues. This is the basis of BNCT in the treatment process. The overall radiation dose which is delivered to each organ can be expressed in terms of a photon equivalent unit which can be expressed as a total component of a dose with high LET multiplied with weighting factors that depends on the radiobiological effectiveness of each of the components.

Generating selectable drugs having high content of enriched 10-Boron is a significant challenge in BCNT. The produced drugs have to be nontoxic for being effective in the treatment and also it ought to have chemotherapeutic properties for destructing the cancerous cells simultaneously as well as being selective and having high content of enriched 10-Boron isotopes. In fact, the overall objective is a simultaneous application of all the influential methods for a certain and perfect destruction of cancer cells. The other significant challenge is that the produced drugs have to be accumulated sufficiently in the intended cell (20 to 35 mcg (micrograms) proportionate to the tumor gram weight). Otherwise it won't result in a sufficient impact for tumor destruction according to the US Patent 2009/0227539A1. The least accumulation ratio of tumor to blood and tumor to healthy tissue should be higher than 5 in these drugs.

Several categories have been used in BCNT. According to the U.S. Pat. No. 5,872,107 nucleotides have been used. The nucleotides, oligonucleotides containing $^{10}$B, nucleosides and oligonucleosides containing phosphorusamides containing $^{10}$B, carboranes, carbonyl pyramidine, purine have been used according to EP 1113020A2. Inorganic compounds containing Boron like borax ($Na_2B_4O_7.10H_2O$), sodium pentaborate ($Na_2B_{10}O_{16}.10H_2O$) were not very successful because their exposure to the tumor cells was not much. Also in the composition of prophyrin containing 10-Boron the ratio of tumor to the normal cell is 4 to 1. However this composition is not suitable for being used in BNCT, due to the fact that a mortality rate of mice was high due to the injection of the drug. All the other compositions applied in this regard with less successful results are monoclonal and polyclonal antibodies, encapsulating complexes like liposomes, microspheres and lipoproteins with low density according to U.S. Pat. No. 6,037,490.

Two compositions of Disodium mercapto-closo-dode-carborate (BSH) and 1-4-dihydroxyborulphenylalanine (BPA) are clinically used in the BNCT method. Although these compositions had good results regarding toxicity and impact, both the factors had medium selectability and also exhibited a low-retention time in the animal models. On the other hand, they either have low chemical residence time in terms of their structure or they have a low content of enriched 10-Boron isotopes. For instance, it was mentioned that either BSH tends to be oxidized when exposed to air or Boron has formed 5% of molecular weight of BPA. Therefore, the researches in the field of the production of compositions containing high levels of 10-Boron would not be toxic and will have aggregation and proper retention time in the cancerous cells and regarding the structure it has proper chemical residence which has remained as a difficulty. The researchers have presented various solutions for solving the problem of selectability. For example Mark. A. Green et al., has illustrated that folate receptors and all the other compositions containing these receptors for therapeutic purposes can be applied according to US2011/0028714A1.

Other researchers have proposed the application of superficialized modified liposome with immune system deceiver compositions like PEG with different molecular weights as mentioned in EP 87311040.7. The other suggestions include the application of methods based on gene, antigen and antibody. A new solution in this regard is the application of the strategy of food supplements. In fact considering the nature of BNCT method i.e. explosion at the cell dimension level as the result of collision of low-energy thermal neutrons with the compositions containing plenty/sufficient amount of $^{10}$B aggregated in tumor cells, a type of cancerous cells can be deceived through cell nutrition mechanisms. So the cell will swallow a drug tumor cell or compositions containing the high levels of 10-Boron content which is bonded with a food composition. By this strategy, firstly the cell tends to bring much more drug containing high levels of 10-Boron into itself and secondly the retention time in tumor cell will increase. The other property of this strategy is that the food supplement compositions can be used in the production of the drug (in this case, the problem of toxicity has been solved automatically). The compositions containing Boron can be found in the bacterial antibiotics such as borophycin, boromycin, aplasmocyn, tarerolon.

Although the currently available methods for treating the tumors are able to satisfy a few needs of the human community, solving this global dilemma remained as an unresolved puzzle. Usage of the chemical drugs, radioactive and radiotherapy applications are of the common methods used for treating cancer. However, not only those methods are not sufficient, but also there is a long way that has to be passed by them. Using the method of Boron Neutron Capture Therapy (BNCT) with $^{10}$B-enriched drug is a novel method in treating the cancerous tumors. The Boron Neutron Capture Therapy (BNCT) has been developed in twentieth century with the growth of technology. Several studies have been carried out in the field of development of necessary instruments and $^{10}$B-supplier drugs and also the quality and amount of this drug. Hence there is a need to develop a composition for an effective and successful treatment of cancer using the Boron Neutron Capture Therapy (BNCT).

The above mentioned shortcomings, disadvantages and problems are addressed herein and which will be understood by reading and studying the following specification.

OBJECTIVES OF THE EMBODIMENTS

The primary object of the embodiments herein is to provide novel methods in the treatment of cancerous tumors using the multiple methods of chemotherapy and radio therapy using a $^{10}$B-enriched drug for applying a targeted drug delivery to a tumor site.

Another object of the embodiments herein is to provide a drug composition comprising large and sufficient content of enriched 10-Boron to be applied in Boron Neutron Capture Therapy (BNCT) for a treatment of cancer.

Yet another object of the embodiments herein is to design and synthesis a composition influential in BNCT method of cancer treatment.

Yet another object of the embodiments herein is to provide a drug with 10-Boron isotopes as vector and having a high content of enriched 10-Boron isotopes with a capability of being delivered to the cells of given tumors selectively.

Yet another object of the embodiments herein is to provide a drug composition that is non-toxic and provides a proper chemical resistance.

Yet another object of the embodiments herein is to provide a drug composition that can be applied in BNCT method and in biological investigations including drug toxicity, suitable dose, its chemotherapy effects and also the drug's biological distribution.

Yet another object of the embodiments herein is to provide a composition which applies both chemotherapy effects of the produced drug and the radiotherapy effects in BNCT method for the treatment of cancer in order to remove cancerous tumors thoroughly and sustainably.

Yet another object of the embodiments herein is to provide a drug composition that is economic and has a reduced cost of production.

Yet another object of the embodiments herein is to provide a drug composition that has minimum side effects.

Yet another object of the embodiments herein is to provide a simple and efficient method of synthesizing a drug composition containing enriched 10-Boron sugar complex.

These and other objects and advantages of the embodiments herein will become readily apparent from the following detailed description taken in conjunction with the accompanying drawings.

SUMMARY

The various embodiments herein provide a novel drug for a treatment of cancer cells and a method of synthesizing the novel $^{10}$B-enriched drug. The embodiments herein also provide a method of treating cancer using a Boron Neutron Capture Therapy.

According to one embodiment herein, a method of synthesizing an enriched 10-Boron complex for Boron Neutron Capture Therapy (BNCT) comprises dissolving a monosaccharide in a solvent at a room temperature while stirring. The solvent may be water or alcohol and the monosaccharide is selected from a group consisting of glucose and a fructose. A solution of an enriched $^{10}$B boric acid is added to form a mixture. A pH of the mixture is adjusted to be equal to 3-4. A solution of a carbonate salt of calcium is added to the mixture while continuously stirring. The solution of the carbonate salt of calcium is added after completely exhausting a carbon dioxide gas produced in the mixture. A bi-phase solution is formed. The bi-phase solution comprises a lower phase and an upper phase. The lower phase is a boron complex and the upper phase is an oily liquid. The lower phase is separated by scratching using a glass bar. The lower phase is collected and grinded to obtain a final preparation. The composition is Enriched 10-Boron Calcium Fructo Borate (E$^{10}$BCFB). The enriched 10-Boron complex has a formula A and a formula B:

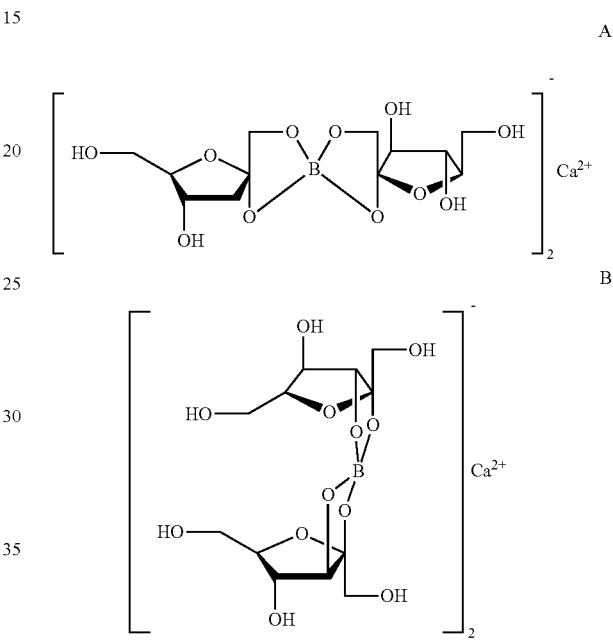

The monosaccharide is dissolved in the solvent to make up a concentration of 1 mole. The solution of the enriched $^{10}$B boric acid is has a concentration of 0.5-1 moles. The composition is applied orally and parenterally.

According to another embodiment herein, a Novel Drug Containing 10-Boron for Cancer Cells Treatment in Smart Boron Neutron Capture Therapy comprises an Enriched 10-Boron Calcium Fructo Borate (E$^{10}$BCFB) having a Formula A:

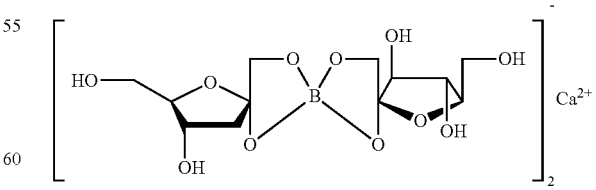

The enriched 10-Boron Calcium Fructo Borate (E$^{10}$BCFB) has a Formula B:

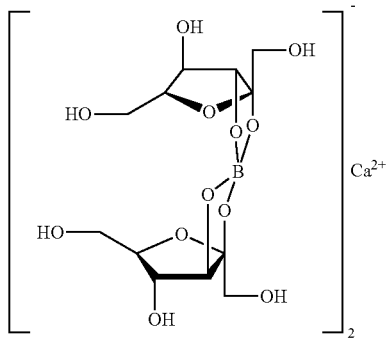

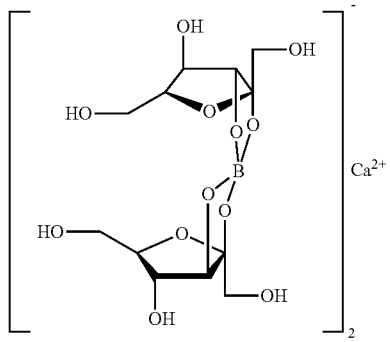

According to one embodiment herein, a method of treating cancer using Boron Neutron Capture therapy comprises administering a novel drug containing compound to a patient. The novel drug containing compound is Enriched 10-Boron Calcium Fructo Borate ($E^{10}BCFB$). A predetermined concentration of the novel drug containing compound is delivered to a tumor site. The delivered novel drug containing compound is accumulated in the cancerous cells. The cancer cells are bombarded from outside using the thermal and epithermal neutron beams. The cancer cells are destroyed when the thermal and epithermal neutron beams comes in to contact with the Enriched 10-Boron Calcium Fructo Borate ($E^{10}BCFB$). The composition is applied orally and parenterally. The predetermined concentration in tumor is 20 mcg $^{10}B/g$ to 35 mcg $^{10}B/g$.

The embodiments herein provide a method of synthesizing a Boron-sugar complex containing composition for treatment of cancer. The method comprises dissolving a monosaccharide in a solvent at a room temperature while stirring. An acid is added while stirring to form a mixture. A solution of an alkali salt is added to the mixture while continuously stirring to obtain a bi-phase solution. The solvent is water or alcohol. The monosaccharide is a fruit sugar. The acid is enriched $^{10}B$ boric acid. The solution of the alkali salt is added after a produced carbon dioxide gas expels out completely. The bi-phase solution comprises a lower phase and an upper phase. The lower phase is a Boron complex and the upper phase is an oily liquid. The lower phase is collected and purified after discharging the upper phase. The monosaccharide is dissolved in the solvent to make up a concentration of 1 mole. The enriched 10-boric acid is added in an amount to form a concentration of 0.5 moles. The mixture has a pH in a range of 3-4. The alkali salt is calcium carbonate. The composition is applied orally and parenterally. The composition is Enriched Boron-10 Calcium Fructo Borate ($E^{10}BCFB$).

According to the embodiments herein, the 10-Boron complex has a formula as shown by A and B:

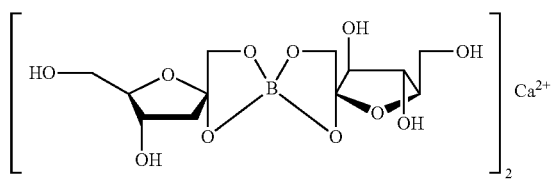

The complex is Enriched 10-Boron Calcium Fructo Borate ($E^{10}BCFB$).

According to one embodiment herein, the sugar is Fructose.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
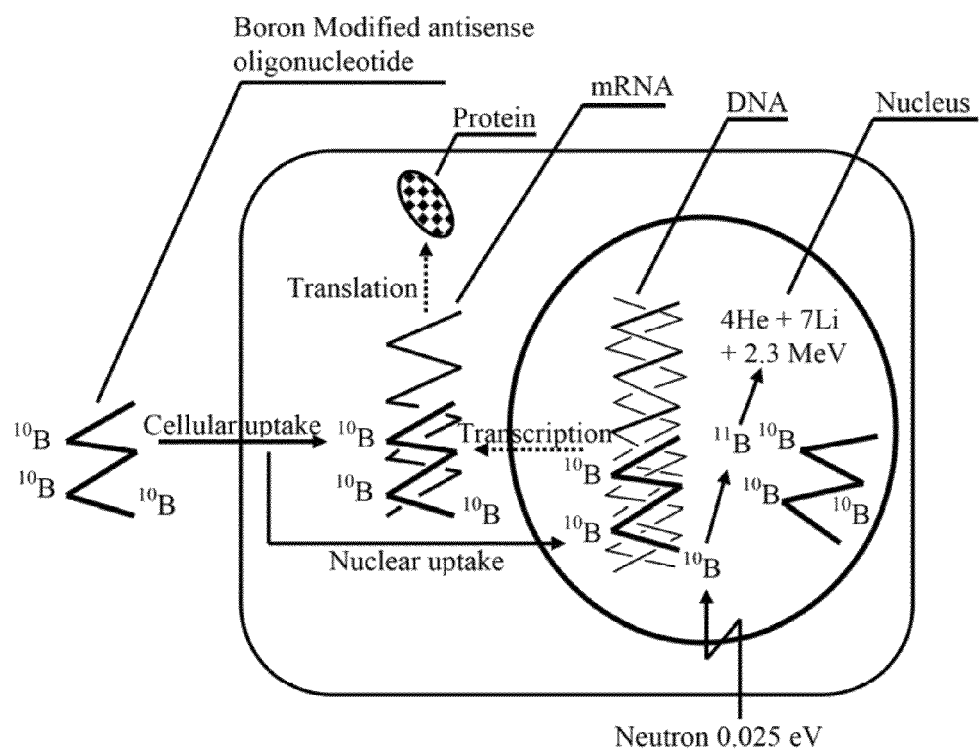
FIG. 1 shows an overall schematic view of the process of the entrance of the drug and the process of Boron Neutron Capture Therapy (BNCT) used in prior art.
Figure 2:
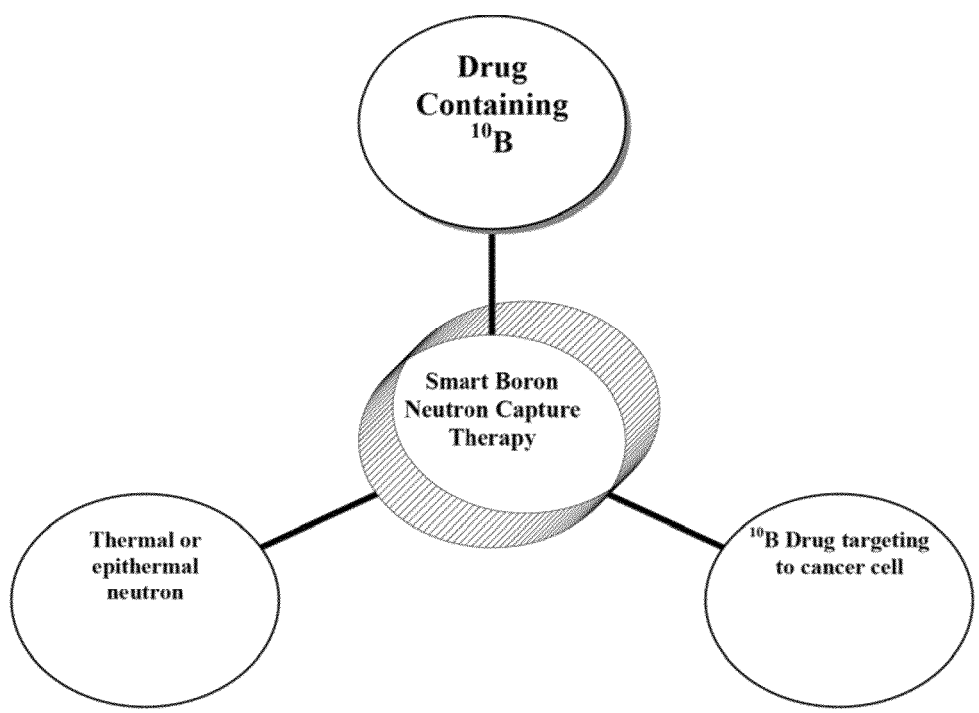
FIG. 2 shows a block diagram showing the various component required in purposeful Boron Neutron Capture Therapy (BNCT) according to a prior art.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a novel drug containing composition for treatment of cancer cells and a method of synthesizing the novel drug containing composition. The embodiments herein also provide a method of treating cancer using Boron Neutron Capture Therapy (BNCT).

According to one embodiment herein, a method of synthesizing an enriched 10-Boron complex for Boron Neutron Capture Therapy comprises dissolving a monosaccharide in a solvent at room temperature while stirring. The solvent is water or alcohol and the monosaccharide is selected from a group consisting of glucose and a fructose. A solution of an enriched $^{10}B$ boric acid is added to form a mixture. A pH of the mixture is adjusted to 3-4. A solution of a carbonate salt of calcium is added to the mixture while continuously stirring. The solution of the carbonate salt of calcium is added after a produced carbon dioxide gas completely expels out from the mixture. A bi-phase solution is formed. The bi-phase solution comprises a lower phase and an upper phase. The lower phase is a boron complex and the upper phase is an oily liquid. The lower phase is separated by scratching using a glass bar. The lower phase is collected and grinded to obtain a final preparation. The composition is enriched 10-Boron Calcium Fructo Borate ($E^{10}BCFB$). The enriched 10-Boron complex has a formula A and a formula B:

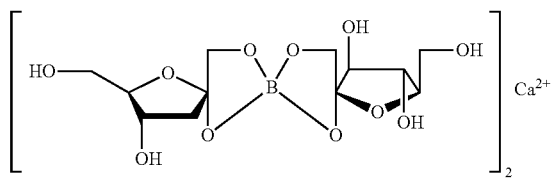

A

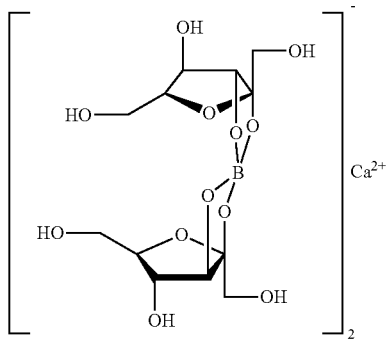

B

The monosaccharide is dissolved in the solvent to make up a concentration of 1 mole. The solution of the enriched $^{10}$B boric acid is with a concentration of 0.5-1 moles. The composition is applied orally and parenterally.

According to another embodiment herein, a Novel Drug Containing 10-Boron for Cancer Cells Treatment in Smart Boron Neutron Capture Therapy comprises an enriched 10-Boron Calcium Fructo Borate (E$^{10}$BCFB) having a Formula A:

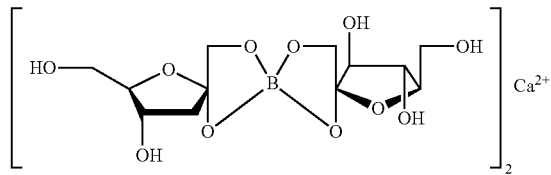

A

The Enriched 10-Boron Calcium Fructo Borate (E$^{10}$BCFB) has a Formula B:

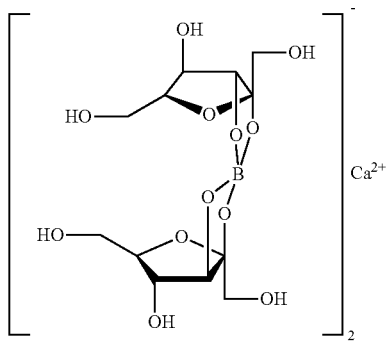

B

According to one embodiment herein, a method of treating cancer using Boron Neutron Capture therapy comprises administering a novel drug containing compound to a patient. The novel drug containing compound is enriched 10-Boron Calcium Fructo Borate (E$^{10}$BCFB). A predetermined concentration of the novel drug containing compound is delivered to a tumor site. The delivered novel drug containing compound is accumulated in cancerous cells. The cancer cells are bombarded from outside using thermal and epithermal neutron beams. The cancer cells are destroyed when the thermal and epithermal neutron beams comes in contact with the Enriched 10-Boron Calcium Fructo Borate (E$^{10}$BCFB). The composition is applied orally and parenterally. The predetermined concentration is 20 mcg $^{10}$B/g to 35 mcg 10B/g.

The embodiments herein provide a method of synthesizing a Boron-sugar complex containing composition for treatment of cancer. The method comprises dissolving a monosaccharide in a solvent at room temperature while stirring. An acid is added while stirring to form a mixture. A solution of an alkali salt is added to the mixture while continuously stirring to obtain a bi-phase solution. The solvent is water or alcohol. The monosaccharide is a fruit sugar. The acid is enriched $^{10}$B boric acid. The solution of the alkali salt is added after a produced carbon dioxide gas expels out completely. The bi-phase solution comprises a lower phase and an upper phase. The lower phase is a 10-Boron complex and the upper phase is an oily liquid. The lower phase is collected and purified after discharging the upper phase. The monosaccharide is dissolved in the solvent to make up a concentration of 1 mole. The enriched $^{10}$B boric acid is added in an amount to form a concentration of 0.5 moles. The mixture has a pH in a range of 3-4. The alkali salt is calcium carbonate. The composition is applied orally and parenterally. The composition is Enriched Boron-10 Calcium Fructo Borate (E$^{10}$BCFB).

Figure 3:
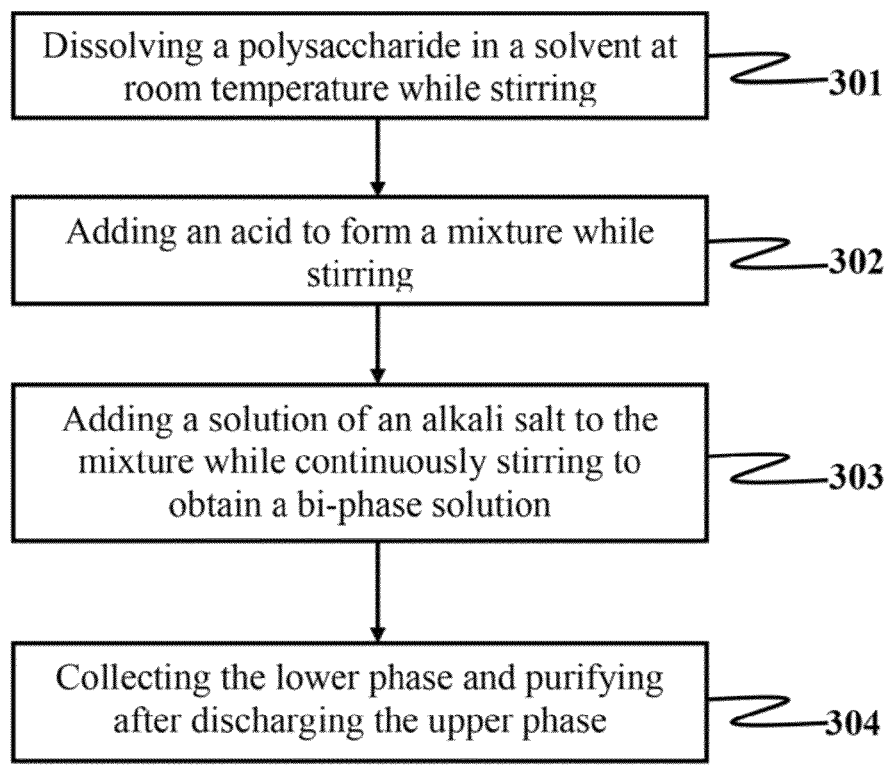
FIG. 3 shows a flow chart indicating the various steps of synthesizing the drug composition according to an embodiment herein.

FIG. 3 is a flow chart showing the various steps of synthesizing the drug composition according to an embodiment herein. With respect to FIG. 3, a method of synthesizing a 10-Boron-fruit sugar complex containing composition for treatment of cancer comprises dissolving a monosaccharide in a solvent at room temperature while stirring (301). An acid is added while stirring to form a mixture (302). A solution of an alkali salt is added to the mixture while continuously stirring to obtain a bi-phase solution (303). The solvent is water or alcohol. The monosaccharide is a fruit sugar. The acid is enriched $^{10}$B boric acid. The solution of the alkali salt is added after a produced carbon dioxide gas expels out completely. The bi-phase solution comprises a lower phase and an upper phase. The lower phase is a 10-Boron complex and the upper phase is an oily liquid. The lower phase is collected and purified after discharging the upper phase (304). The monosaccharide is dissolved in the solvent to make up a concentration of 1 mole. The enriched $^{10}$B boric acid is added in an amount to form a concentration of 0.5 moles. The mixture has a pH in a range of 3-4. The alkali salt is calcium carbonate. The composition is applied orally and parenterally. The composition is Enriched 10-Boron Calcium Fructo Borate (E$^{10}$BCFB).

The 10-Boron complex has a formula as shown by A and B:

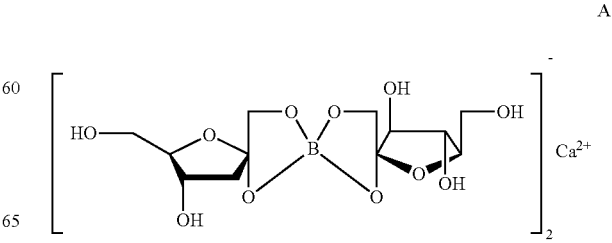

A

-continued

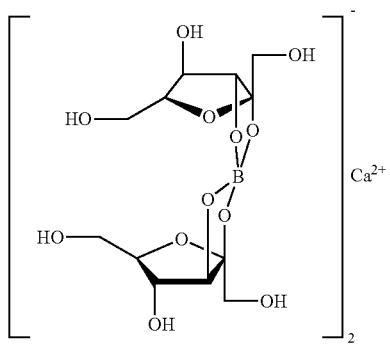

According to one embodiment herein, the sugar is Fructose.

According to another embodiment herein, the sugar is a fruit sugar.

The embodiments herein provide a design and construction of new compositions containing large and sufficient content of 10-Boron isotopes to be applied in Boron Neutron Capture Therapy (BNCT) method. The methods and composition construction is inspired by Boron-contained compositions found in the nature, design methods, making the intended drug smart and its synthesis using receptors specific to biological and clinical studies of these drugs, dealing with toxicity and their biological distribution and launching clinical studies. In designing this drug it has been tried to exploit both the chemotherapy effects of the produced drug and radiotherapy effects in BNCT method in order to remove cancerous tumors thoroughly and sustainably. Regarding economic considerations to reduce production cost as well as minimum side effects in treatment are among other advantages of the applied drug and method.

Neutron therapy includes treatment through capturing neutron using absorbent compositions of neutron enjoying large capture neutron cross section for instance sustainable 10-Boron is indeed a type of radiotherapy—chemotherapy methods for treating tumors which has considered both aspects of chemotherapy and radiotherapy.

According to the embodiments herein, the synthesized composition is given to a patient's body through intra venous injection. The produced drug can be given to the body through I.P, I.V, and oral methods. This composition can also be used through pharmacological vectors such as saline.

EXPERIMENTAL DATA

Production of the Drug and Testing Methods

The therapeutic tests using drugs containing 10-Boron isotope according to the embodiments herein were divided into two categories. The first category is the synthesis of drug containing enriched 10-Boron and determining its properties. The second category includes the tests carried out on the investigation of the drug's deterrent effect in in vitro and in vivo circumstances on laboratory animals bearing tumors.

Variety of treatment methods were used for cancer cells. Among them, Boron Neutron Capture Therapy (BNCT) is the promising method that developed in the last few years. In BNCT, drug containing enriched 10-Boron has the important role in final treatment efficiency. In this research, a new smart drug, Enriched Boron-10 Calcium Fructo Borate ($E^{10}BCFB$), was investigated for using in cancer cells treatment in BNCT methods. The Calcium Fructo Borate (CFB), which is found in some vegetables, may also be used in food supplements and as a pharmaceutical ingredient with effects in oxidative metabolism and cell apoptosis. $E^{10}BCFB$ is in fact an artificial Calcium Fructo-Borate which is synthesized chemically with 10-Boron. The reason behind accumulation of $E^{10}BCFB$ in tumor tissues is the overexpression of fructose transporter GLUT5 in tumor cells. This is how metabolism in cancerous cells works. Cancerous cells lose the inhibitory factors that blocks intensive GLUT5 expression in normal cells. $E^{10}BCFB$ becomes an important competitor drug in the fight against some cancerous cells. $E^{10}BCFB$ enters inside cancerous cells and induces a pro-apoptosis effect that enhances the BNCT effect. Four different methods with specific methodology exist when using Boron chemistry against cancer cells: diet-based chemoprevention, chemotherapy, radiotherapy and Smart BNCT. In the embodiments herein, in vitro and in vivo tests results with $E^{10}BCFB$ drug on cancerous mice showed that this drug is safe and excellent for BNCT method compared with previous drugs.

The prepared drug is applied on the patient orally or parenterally by means of oral serum solutions in different turns to reach to the needed doze. Three hours after the injection the drug is accumulated in tumor so that the patient is ready for radiation. The patient receives the thermal neutron through radiation and the treatment process is completed.

Since this drug has been tested on breast cancer cells MDA-MB-231, it has a preventing effect on these cells and it is entered into cells via aided transfer mechanism with sugar carriers. Then, it functions as an antioxidant and obstructs the proteins that are active in apoptosis and finally stops the apoptosis. On the other hand, one of the components of the drug prevents the cells' proliferation, but does not kill them. The anti-proliferation mechanism of the drug is not known yet. Treating the tumor cells with this drug leads to quick release of Cytochrome C from Mitochondria and this increases the Caspase-3 activity. Consequently this drug prevents the growth of breast cancer cells. Besides this, the drug comprising Boron-10 isotopes that is practical in BNCT treatment. Consequently, the synthesized drug according to the embodiments herein is efficient via BNCT method.

Synthesis of Boron Containing Enriched 10-Boron Isotope

Example 1

In order to make the Enriched 10-Boron Calcium Fructo Borate ($E^{10}BCFB$), 1 molar fructose is dissolved in water or Ethanol. This reaction should be done in room temperature while it is stirred. Then, some Boric Acid containing enriched 10-Boron isotope is added to the solution in a way that the total density of enriched $^{10}B$ Boric Acid reaches to 0.5 molar. On the other hand, by adding enriched $^{10}B$ Boric Acid, the pH of the reaction container goes down until it reaches to 3-4. The pH should be checked regularly by a pH meter. After adding enriched 10-Boron Boric Acid, a little Carbonate salt of solid Calcium is dissolved in a little amount of water and added to the reaction container. The reaction environment should be empty of $CO_2$ gas before adding the Carbonate solution. Then stirring is stopped and the solvent is taken out of the environment with a vacuum pomp or Lyophilisation system. Along the process of this composition, after adding the Carbonate solution which does not have any $CO_2$, a biphasic solution is formed. The lower phase is Enriched 10-Boron Calcium Fructo Borate complex ($E^{10}BCFB$) and the upper phase is greasy liquid. The lower phase is separated and filtered via a Buchner funnel. After filtering, it is gathered by a glass bar for crystallization. Finally, this composition is kept for the next steps.

A and B shows the molecular formula of the Enriched 10-Boron Calcium Fructo Borate complex ($E^{10}BCFB$):

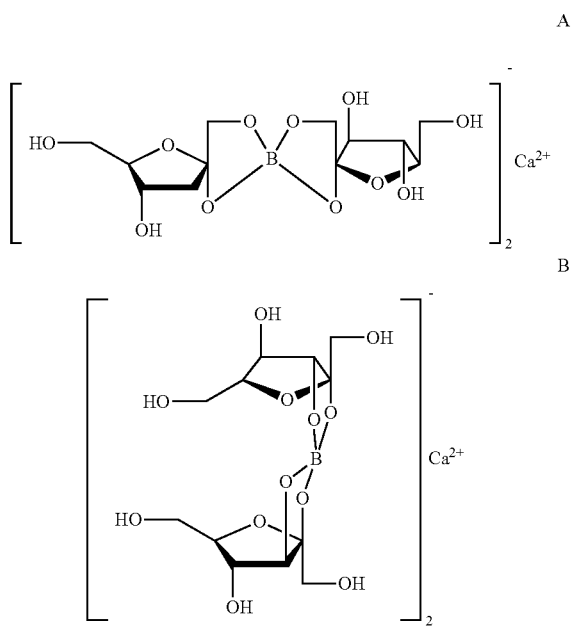

Synthesis of the New Composition Using Enriched 10-Boron Isotopes

Sugar was solved in either in aqueous environment or ethanol with 1 molar final concentration. The reaction was carried out at the room temperature as the mixture was being stirred. Then an amount of $^{10}B$ boric acid was added to it. The boric acid is enriched and has high content of $^{10}B$ isotope. The overall concentration of enriched $^{10}B$ boric acid should be 0.5 molar. On one hand, the pH of the reaction container decreases as enriched $^{10}B$ boric acid is added and reaches to 3-4 which should constantly be controlled by pH meter. After enriched $^{10}B$ boric acid was added, an amount of sodium carbonate of solid calcium was solved in small amount of water and then was added to the reaction environment. Before adding carbonate solution, the generated $CO_2$ gas should exits from the environment. The stirring was stopped and the solvent was discharged either through a powerful vacuum pump or a lyophilization system. During the process of formation of composition, a two-phase solution was generated after the addition of soluble carbonate whose $CO_2$ gas has been discharged, the lower phase was the Boron complex and the upper phase was an oil-form liquid. The lower phase was isolated and was thoroughly sieved through a Büchner funnel. After being sieved, it was collected by a glass rod and the crystallization process was carried out. Then, the formed composition was collected and was kept for the next stage.

Example 2

Providing 1 molar solution of Fructose in water or Ethanol. Providing a Boric Acid containing enriched 10-Boron. Providing 1 and 0.5 molar solutions of Boric Acid containing enriched 10-Boron. Adjusting and controlling the solution pH around 3-4 (solution 1). Adding some Carbonate salt of solid Calcium (dissolved in a little amount) to solution 1. Formation of biphasic solution and separation of the lower phase. Scratching the lower phase with a glass bar. Formation of Calcium Fructo Borate complex containing enriched 10-Boron ($E^{10}BCFB$). Grinding and final preparation.

Figure 4A:
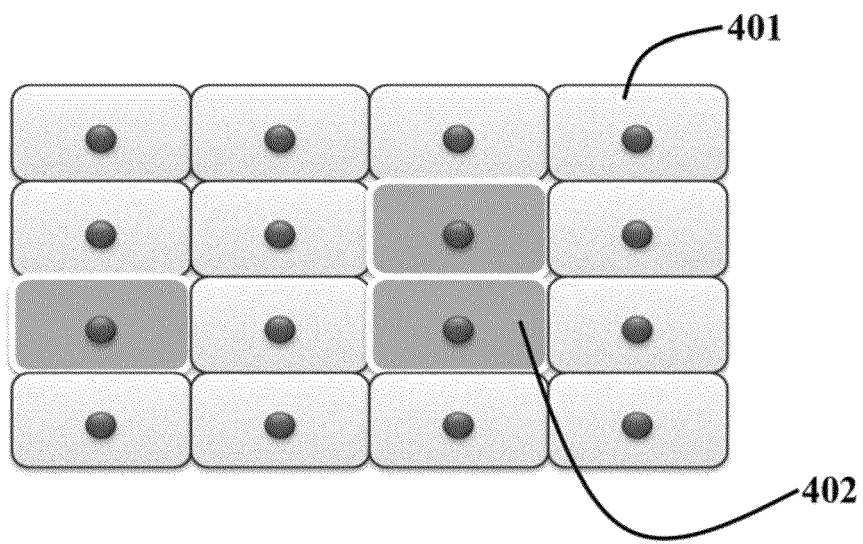
FIG. 4A shows a schematic view of a cancer tissue exhibiting normal and cancer cells.

FIG. 4A shows a schematic view of a cancer tissue showing normal and cancer cells. With respect to FIG. 4A, cancer cells 402 are lying in between the normal cells 401.

Figure 4B:
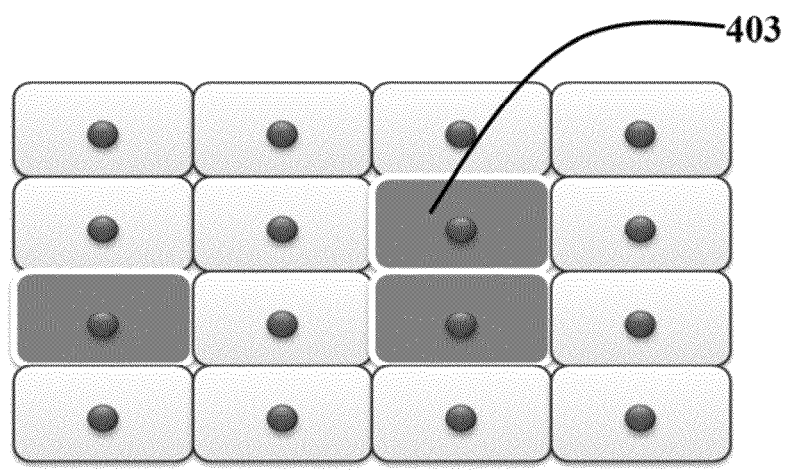
FIG. 4B shows a schematic view of the cancer tissue after injecting and accumulation of the enriched 10-Boron drug as synthesized according to the embodiments herein.

FIG. 4B shows a schematic view of the cancer tissue after injecting and accumulation of the enriched 10-Boron drug as synthesized according to the embodiments herein. With respect to FIG. 4B, the cells 403 has the targeted accumulation of enriched 10-Boron drug after injecting a dose of the synthesized drug according to the embodiments herein.

Figure 4C:
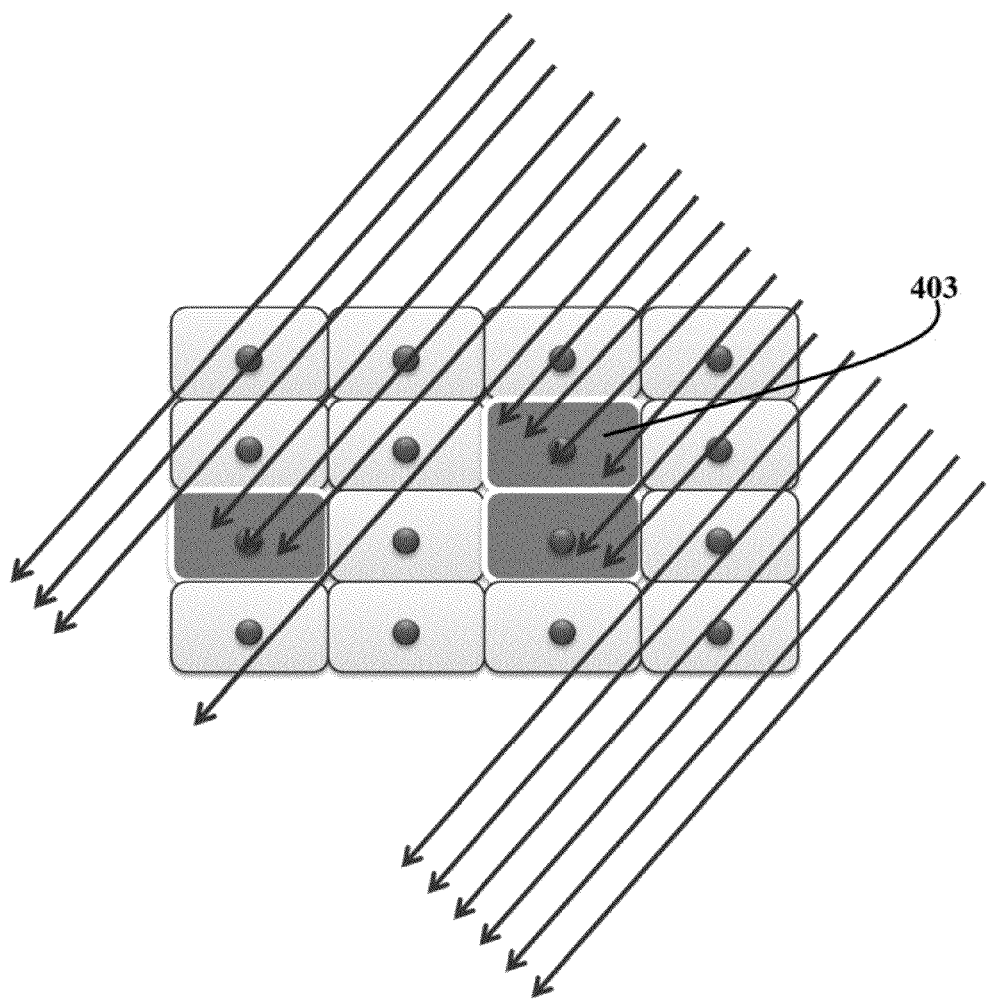
FIG. 4C shows a schematic view of the cancer tissue during a neutron radiation, according to an embodiment herein.

FIG. 4C shows a schematic view of the cancer tissue during a neutron radiation, according to an embodiment herein. With respect to FIG. 4C, the neutron beams are passed through the tissue. The 403 cells absorb the neutrons. The cancer cells 403 have accumulated enriched 10-Boron isotope. 10-Boron isotopes have been a very good absorber of neutrons.

Figure 4D:
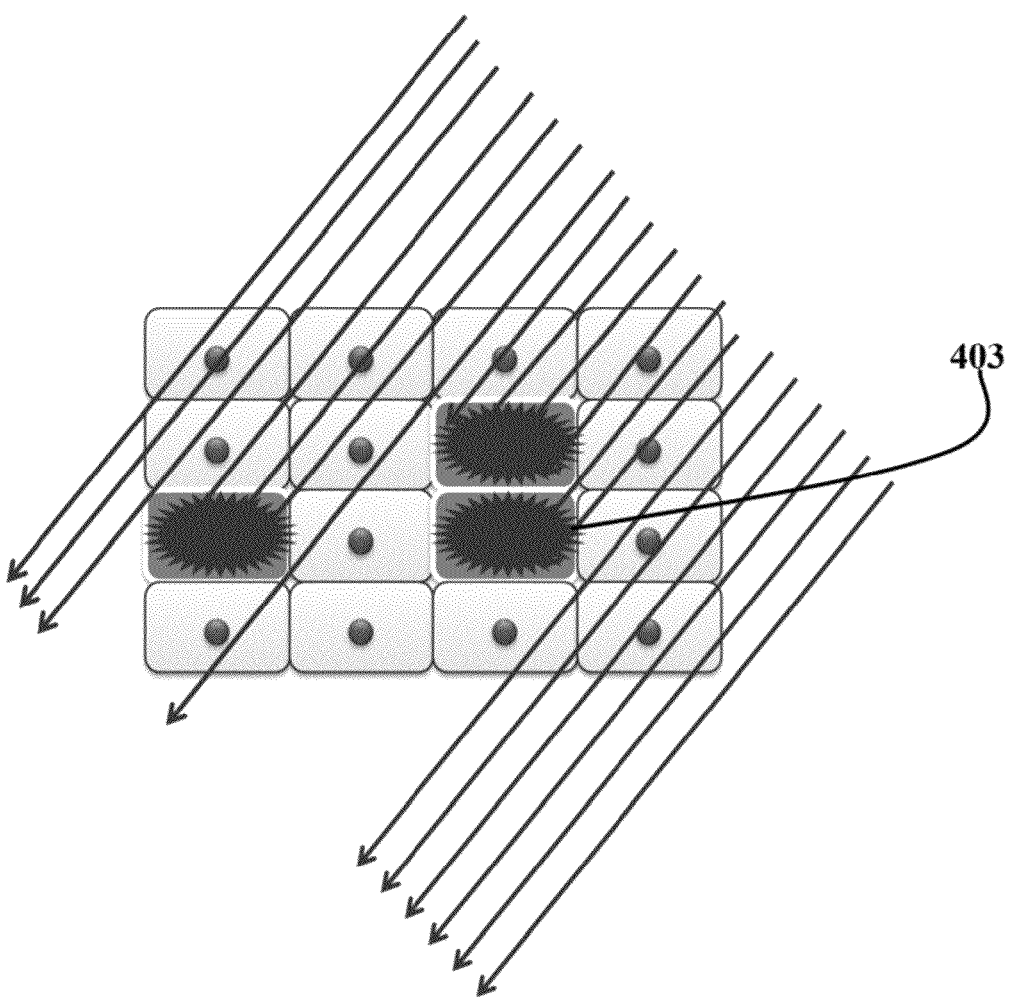
FIG. 4D shows a schematic view of the destruction of the cancer cells using enriched 10-Boron Neutron Capture Therapy (BNCT), according to the embodiments herein.

FIG. 4D shows a schematic view of the destruction of the cancer cells using enriched 10-Boron Neutron Capture Therapy, according to the embodiments herein. With respect to FIG. 4D, the cancer cells 403 due to 10-Boron neutron energy of interaction are destroyed. 10-Boron neutron energy of interaction is very high, but short-range (at least 9 microns (smaller than a cell diameter)). So it does not harm the healthy cells nearby.

Figure 4E:
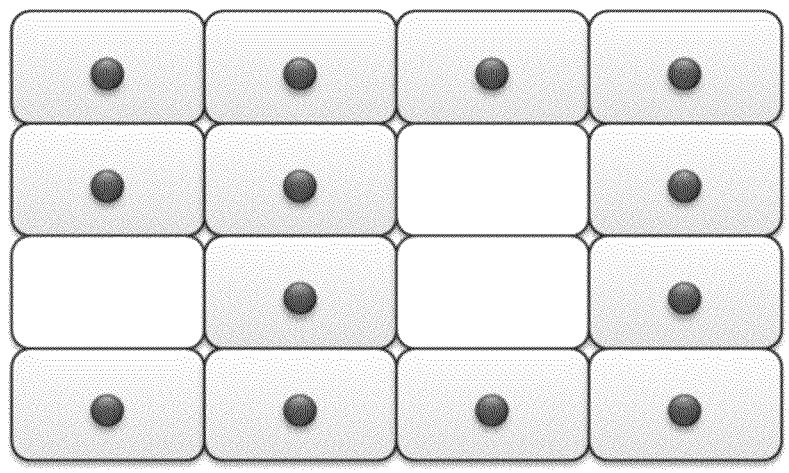
FIG. 4E shows a schematic view of the treated cancer tissue by the drug composition synthesized according to the embodiments herein.

FIG. 4E shows a schematic view of the treated cancer tissue by the drug composition synthesized according to the embodiments herein. With respect to FIG. 4E, after the treatment process, the DNA and some cancer cell organelles are damaged in the reaction. Finally, a programmed cell death pathways are paved and the cell dies.

Figure 4F:
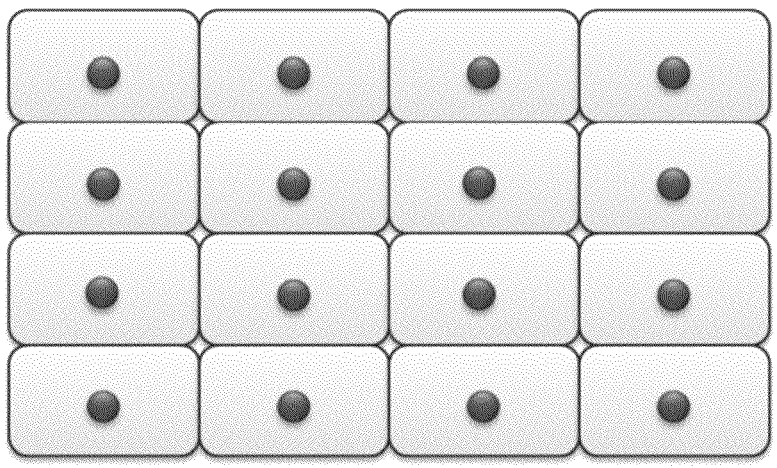
FIG. 4F shows a schematic view of the cancer tissue after the treatment with the synthesized drug composition according to the embodiments herein.

FIG. 4F shows a schematic view of the cancer tissue after the treatment with the synthesized drug composition according to the embodiments herein. With respect to FIG. 4F, the cancer tissue has become a healthy normal tissue. After the passage of time, the dead cells of the body are replaced by healthy cells. The healthy cells further multiply to form a healthy and a normal tissue.

Determination of the Properties of the Synthesized Composition

Fourier Transform Infrared Spectroscopy (FT-IR):

The Fourier Transform Infrared spectroscopy (FT-IR) is one of the most conventional methods which has been applied for analysis and identification of materials and chemical compositions and some of their additives.

For experimenting the synthesized drug composition according to the embodiments herein, the composition was drawn into tablets. The tablets were produced from the samples of the synthesized drug. The FT-IR analysis was performed for the tablets. The infrared spectrum of the samples was obtained in the wavelength range of 400-4000 $cm^{-1}$ through FT-IR device. The model of the used device for studying chemical structure of the compositions was (FT Infrared Spectroscope, JASCO, FT/IR-6300 (400-4000 $cm^{-1}$), Japan) and also it is made in Japan. The Infrared spectroscopy presents useful information about chemical structure of the synthesized materials and of their functional groups. Through dealing with FT-IR spectrums and comparing them in the compositions, the alternations resulted from chemical reactions among the compositions can be found out.

Figure 5:
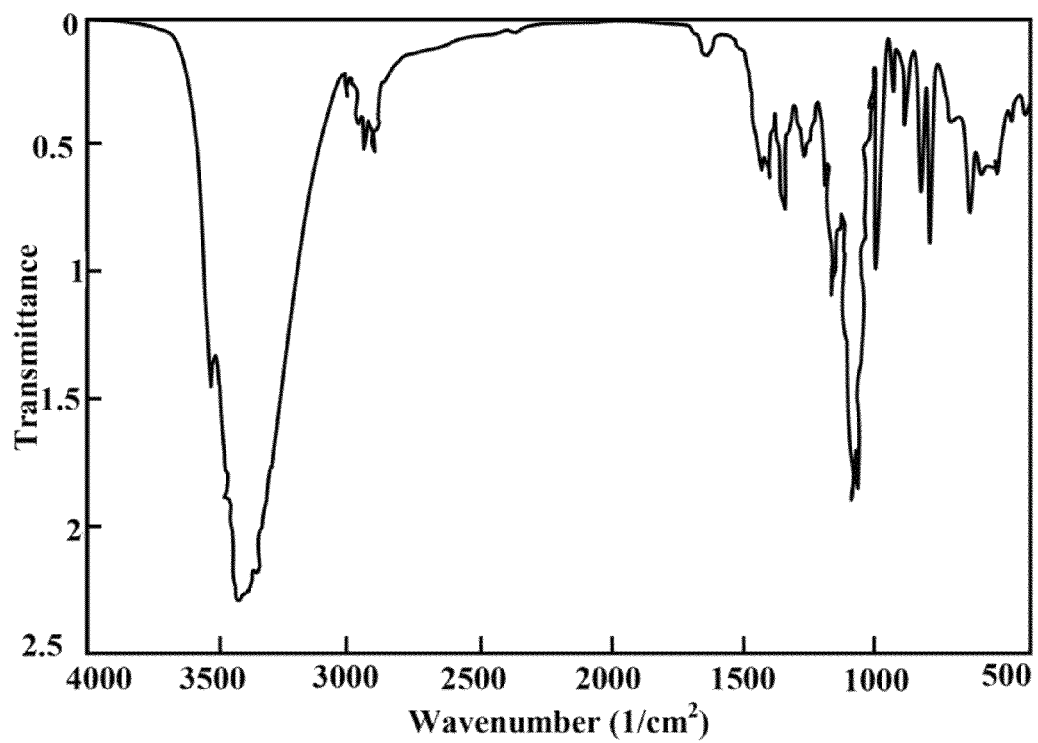
FIG. 5 shows a FT-IR spectrum of the synthesized composition, according to an embodiment herein.

FIG. 5 shows a FT-IR spectrum of the synthesized composition, according to an embodiment herein. With respect to FIG. 5, the composition showed two sharp peaks at 3401 and 3521 cm$^{-1}$. These peaks are attributed to the groups of O—H, CH$_2$OH, OH—H. Two medium peaks are observed at 1427 and 1397 cm$^{-1}$. These peaks are attributed to the attraction of the O—H, CH$_2$OH, OH—H groups. A sharp peak at 1147 cm$^{-1}$ and a medium one is observed at 1250 cm$^{-1}$. These peaks are attributed to C—H and H—C—H groups, respectively. A sharp peak at the frequency of 976 cm$^{-1}$ and a medium peak is observed at 817 cm$^{-1}$ which are attributed to CO and C—C groups, respectively. Another powerful peak is also observed at 781 cm$^{-1}$ which relates to ethereal C—O—C.

Figure 6:
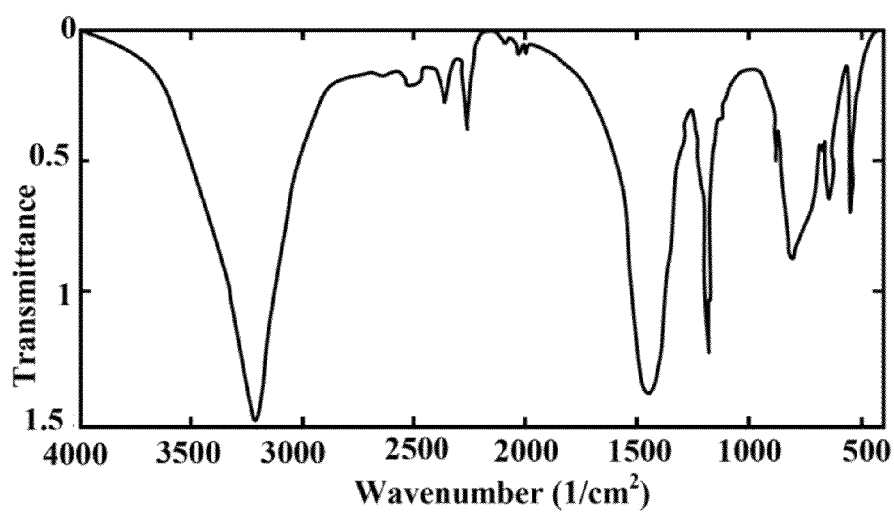
FIG. 6 shows an FT-IR spectrum of from $^{10}B$ boric acid precursor, according to an embodiment herein.

FIG. 6 shows an infrared spectrum of Boron Fourier Transform from $^{10}$B boric acid precursor, according to an embodiment herein. With respect to FIG. 6, in the FT-IR spectrum related to the $^{10}$B boric acid, a sharp peak is observed at 3225 cm$^{-1}$ which is attributed to the stretching vibration of O—H. Another sharp peak is observed at 1455 cm$^{-1}$ relating to asymmetric stretching of tetrahedron structures existing in boric acid. One more peak is also observed at 500-700 cm$^{-1}$ which is attributed to O—B—O ring bendings.

Figure 7:
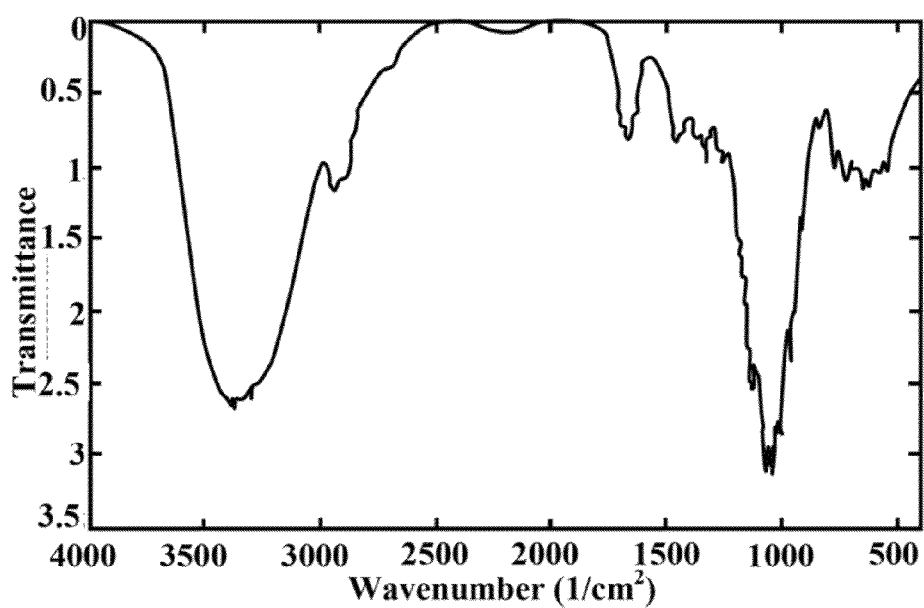
FIG. 7 shows an FT-IR spectrum of synthesized composition using $^{10}B$ accompanied by receptor, according to an embodiment herein.

FIG. 7 shows an infrared spectrum of Fourier transform of synthesized composition using $^{10}$B accompanied by receptor. With respect to FIG. 7, there is a broad high-intensity pick in 3000-3600 cm$^{-1}$ range which relates to both stretching vibrations of O—H group and bending of OH—H group in the receptor structure. The reason maybe the present of high percentage of receptor. However the intensity of these peaks was changed due to the emersion of new interactions in the structure of the composition in the range of 1200-1770 cm$^{-1}$. These peaks related to CH, OH CH$_2$OH, CH$_2$ groups. Some peaks were seen from 600-1050 cm$^{-1}$ which almost overlapped with each other. These are attributed to the vibrations of the groups such as CO, C—CH, C—C, C—O and C.

Figure 8:
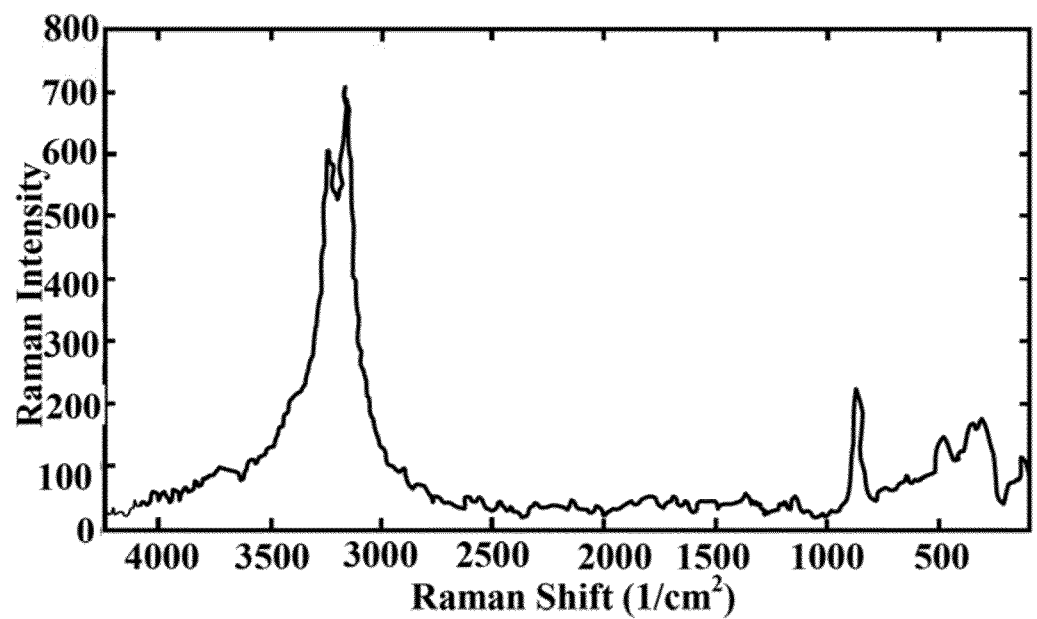
FIG. 8 shows the Raman spectrum of $^{10}B$ boric acid, according to an embodiment herein.

Raman Spectroscopy:

The Raman Spectroscopy with model (Almega Thermo Nicolet Dispersive Raman Spectrometer) with spectrum range of 100-4200 cm$^{-1}$ was applied for dealing with chemical structure of materials and Boron compositions synthesized according to the embodiments herein. FIG. 8 shows the Raman spectrum of $^{10}$B-boric acid, according to an embodiment herein. The Raman transmittance mostly confirms the results of infrared spectrum. With respect to FIG. 8, it was observed in that, one of the high-intensity peak was observed in the range of 3314 cm$^{-1}$ which was attributed to B—O bond. This was observed in the ranges of 3225 cm$^{-1}$ in the FT-IR spectra related to boric acid.

Figure 9:
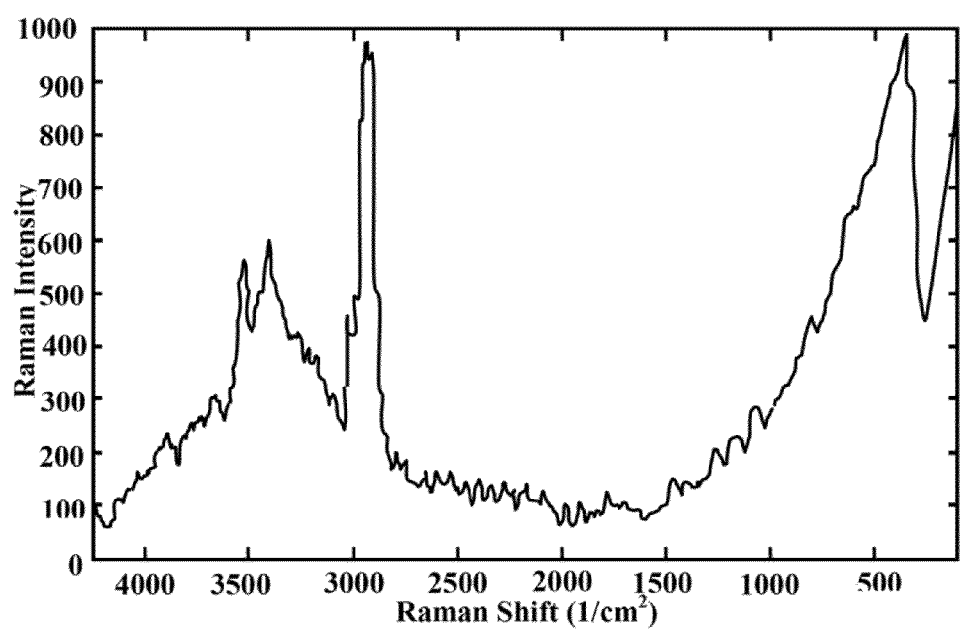
FIG. 9 shows a Raman spectrum of the receptor, according to an embodiment herein.
Figure 10:
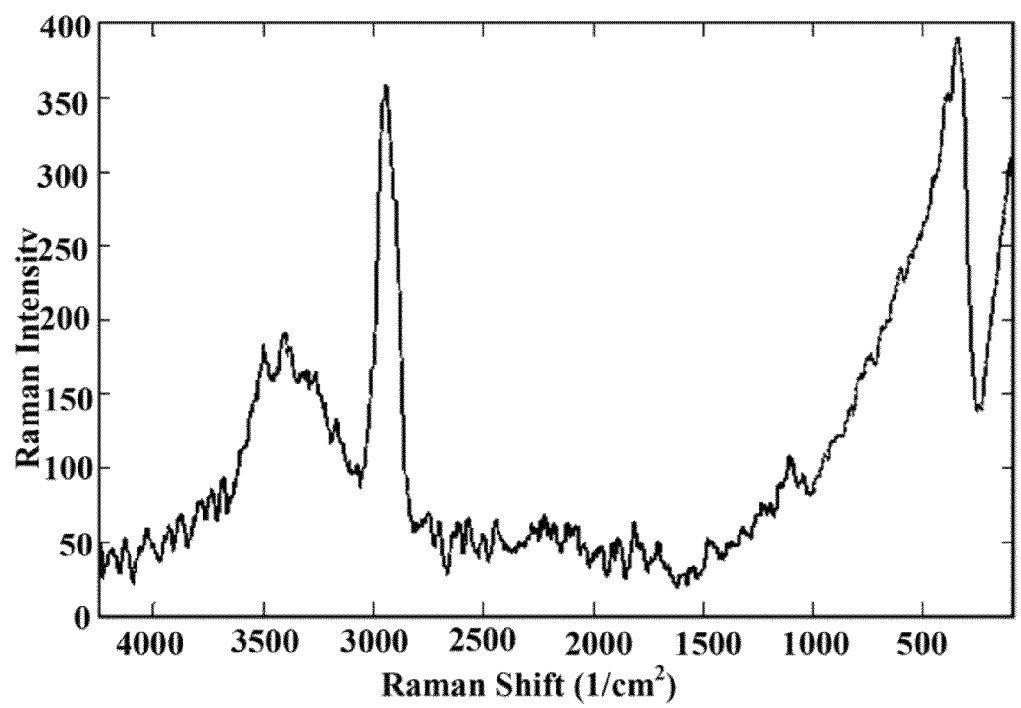
FIG. 10 shows a Raman spectrum of the new composition accompanied by the receptor, according to an embodiment herein.

FIG. 9 shows a Raman spectrum of the receptor, according to an embodiment herein and FIG. 10 shows a Raman spectrum of the new composition accompanied by the receptor. With respect to FIG. 9 and FIG. 10, it can be seen that there is a powerful peak at 3000 cm$^{-1}$ which was shows the presence of the vibrations of CH and CH$_2$OH. This data is visible in FT-IR spectra. A low-intensity broad peak was observed in the range of 3100-3600 cm$^{-1}$ which relates to BO, BO.H$_2$O.OH and CH$_2$OH functional groups. These peaks also were also present in the FT-IR spectra with low intensity and relate to functional groups existing in the receptor structure. A broad intense peak was also observed at the range of 500-1000 cm$^{-1}$ which showed the presence of the CO.H$_2$O and CH$_2$OH groups. These groups exist in the composition structure. The boric acid did not appear greatly in final composition spectra due to the alternations in the structure of the composition.

The results of Fourier transform infrared spectroscopy and Raman scattering illustrated that boric acid changes radically in the synthesis of this composition and the receptor bears little interactions. Thus the structure of the composition would not have significant alternations. Moreover, the results showed that the synthesized composition has high content of receptor in its structure.

Investigating Thermal Behavior of the Synthesis

Figure 11:
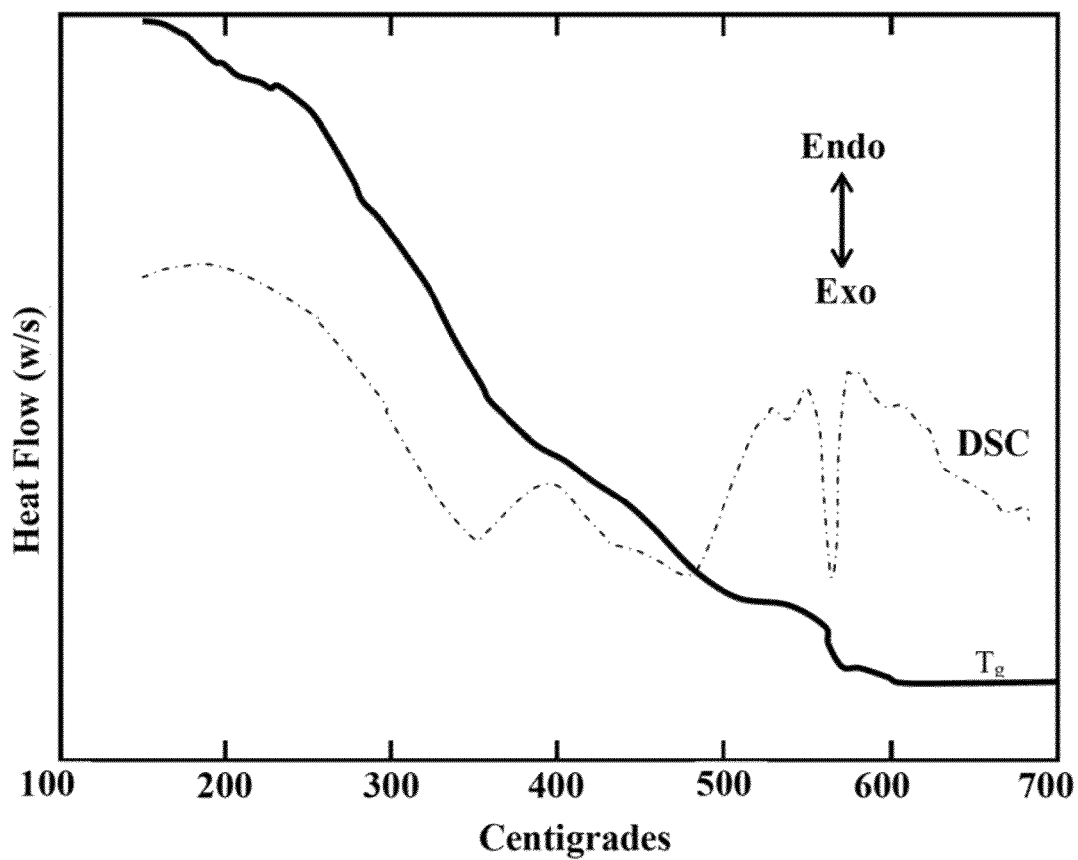
FIG. 11 shows a diagram indicating the thermal behavior of the synthesized composition with $^{10}B$ accompanied by the receptor, according to the embodiments herein.

For dealing with thermal behavior of the synthesized composition, Differential scanning calorimetry (DSC) was applied. FIG. 11 shows a diagram showing the thermal behavior of the synthesized composition with $^{10}$B accompanied by the receptor, according to the embodiments herein. With respect to FIG. 11, it was seen that after synthesis of the composition, none of the precursors of this composition was found in the produced material. This was attributed to the receptor destruction in DSC spectrum in temperature range of 155-580° C. TG results illustrate gradual destruction of the composition mass. This destruction has maximum amounts in temperatures of 570° C., 500° C., 374° C. and 249° C. Regarding the data related to the destruction of mass, it can be said that synthesized composition can have a structure with crystal water molecule in it. The cause can be justified that in initial exothermic stages an endothermic peak was observed in DSC diagram, which often is attributed to water loss of the crystal structure of the composition. Next stage of destruction is named respectively as receptor destruction in the composition and finally formation of borate transform from the remaining of the composition components in the system.

X-Ray Diffraction:

Due to the fact that is applicable in generating Boron containing drug with crystal structure, X-ray diffraction spectroscopy was used for proving the change of the structure of the synthesized composition. The samples were evaluated through XRD apparatus (Diffractometer X-ray Bruker, D8ADVANCE) being made in Germany and its X-ray diffraction spectrum was obtained. The crystal compositions of boric acid, receptor, carbonate precursor and the final composition were evaluated and investigated with using X-ray diffraction spectroscopy. XRD spectra of these compositions are illustrated in FIGS. 12-15.

Figure 12:
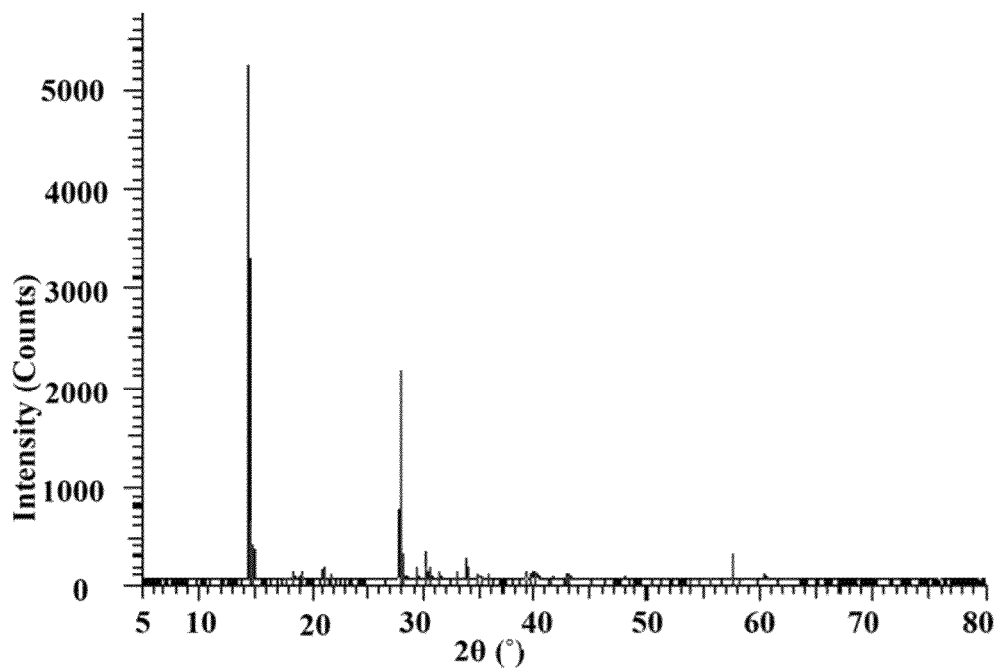
FIG. 12 shows a XRD spectrum of $^{10}B$-boric acid, according to the embodiments herein.
Figure 13:
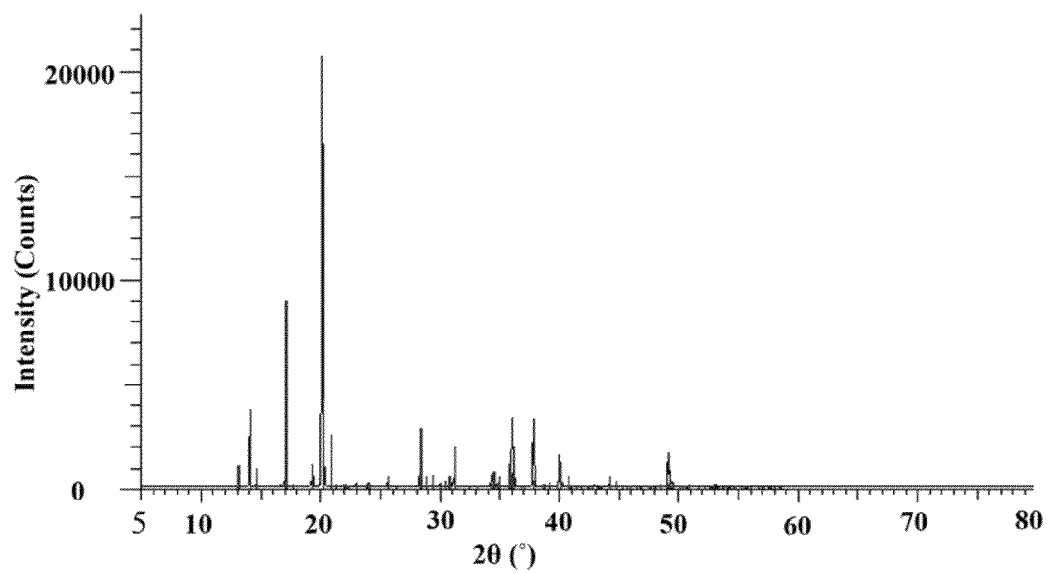
FIG. 13 shows a XRD spectrum of Receptor, according to the embodiments herein.
Figure 14:
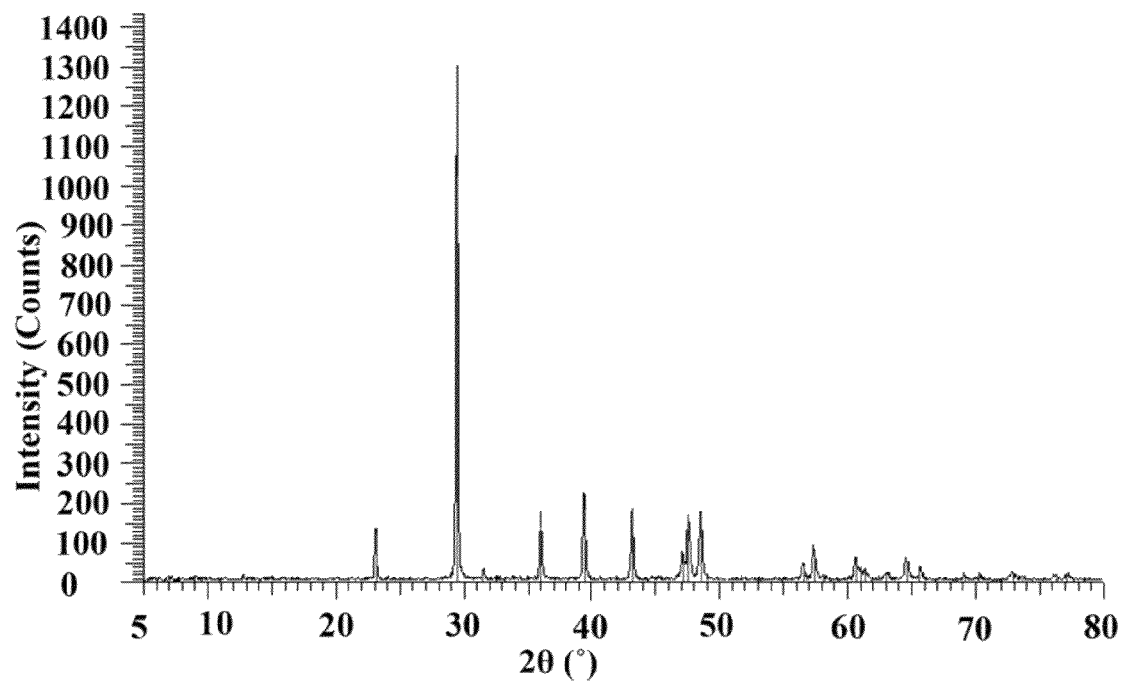
FIG. 14 shows a XRD spectrum of carbonate precursor, according to the embodiments herein.
Figure 15:
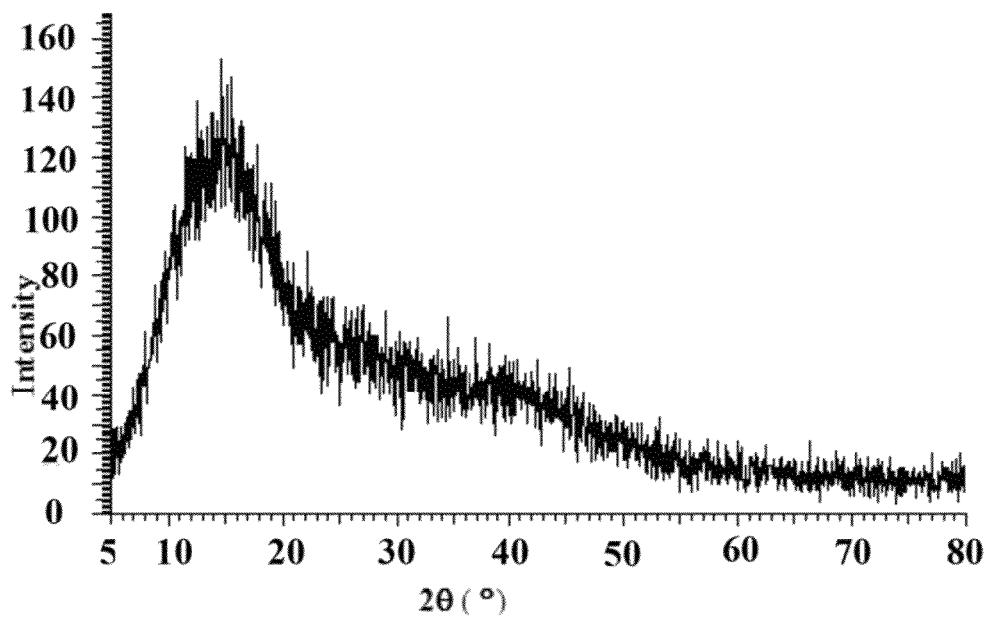
FIG. 15 shows a XRD spectrum of the final composition as well as receptor, according to the embodiments herein.

FIG. 12 shows a XRD spectrum of $^{10}$B-boric acid, according to the embodiments herein. FIG. 13 shows a XRD spectrum of Receptor, according to the embodiments herein. FIG. 14 shows a XRD spectrum of carbonate precursor, according to the embodiments herein. FIG. 15 shows a XRD spectrum of the final composition as well as receptor, according to the embodiments herein. With respect to FIG. 12 to FIG. 15, the XRD data of the composition shows that the composition has low crystallinity. The results illustrate that the most intensive peaks are related to the ranges of 28.14, 19.92, 16.86: θ2. Further the results showing that receptor has major contribution to the composition structure in a way that crystal structure of the final composition is partly affected by its crystal structure.

Induced Couple Plasma (ICP):

ICP apparatus or Induced Couple Plasma, is an elemental analysis system whose spectrometry type is emission spectroscopy and it's method of its atom making is implemented through plasma. Its measurement accuracy is at parts-per notation levels. This apparatus is applied in the study of the elements that are used in small amounts with large applications. In the present study ICP-AES apparatus was used for quantitative measurement of 10-Boron composition amount in the healthy tissues, blood and tumor tissues.

Biological Tests of the Synthesized Composition

In this section, experiments related to the biological tests are carried out. These experiments are fulfilled in conditions of in vivo and in vitro. To put it in nutshell, the performed deeds are as the following:
Dealing with biologic distribution of the designed drugs in different times of injection.
Dealing with biologic distribution of various doses of the drug
Dealing with sufficient accumulation of the designed drug containing enriched 10-Boron aiming at influential treatment of the ray Drug Injection Methods:

The produced drug can be given to the body through I.P, I.V, and oral methods. This composition can also be used through pharmacological vectors such as saline.

Studying the Effects of Drug Containing $^{10}$B on the Malignant Cancerous Cell Line of Breast Cancer and Dealing with the Dose—Response Curve:

MTT assay method was applied for evaluating the effects of Boron complex on MDA-MB241 cell line (malignant breast cells) in in vitro environment.

Figure 16:
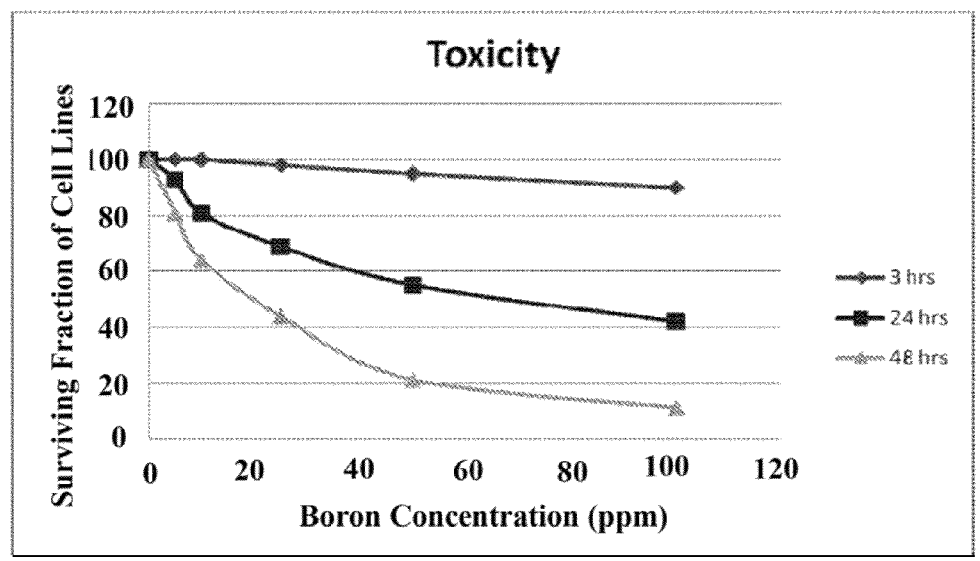
FIG. 16 shows a graphical representation of the toxicity of the synthesized composition using MTT assay method.
Figure 17A:
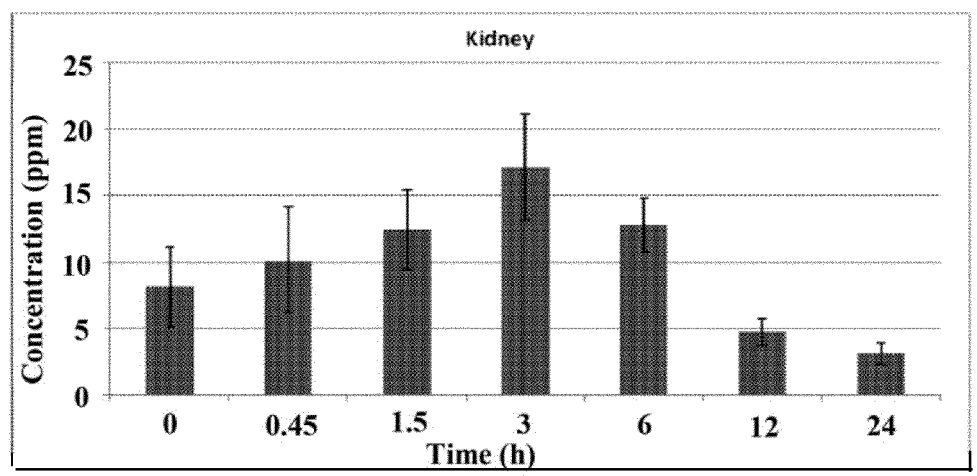
FIG. 17A shows a graphical representation of the biodistribution of the $^{10}B$-Drug in the kidney of the body of the animal model in different times after injection (as per injection of 41.1 mg of enriched 10-Boron complex per every 30 gram of the animal's weight), according to one embodiment herein.
Figure 17B:
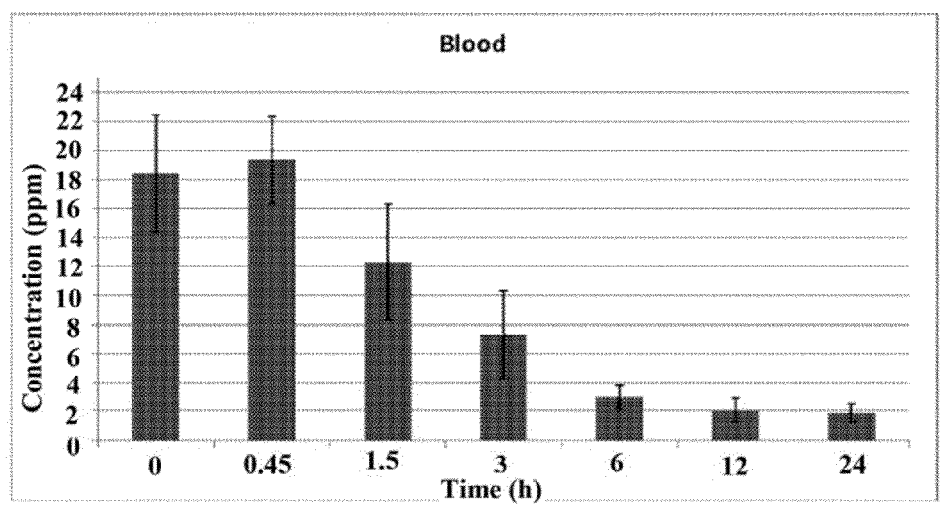
FIG. 17B shows a graphical representation of the biodistribution of the 10B-Drug in the blood of the body of the animal model in different times after injection (as per injection of 41.1 mg of enriched 10-Boron complex per every 30 gram of the animal's weight), according to one embodiment herein.
Figure 17C:
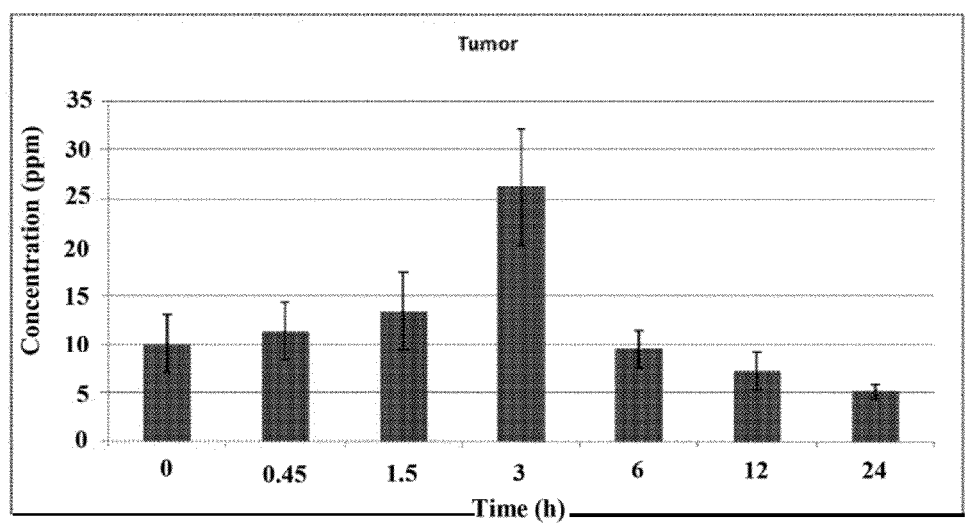
FIG. 17C shows a graphical representation of the biodistribution of the 10B-Drug in the tumor of the body of the animal model in different times after injection (as per injection of 41.1 mg of enriched 10-Boron complex per every 30 gram of the animal's weight), according to one embodiment herein.
Figure 17D:
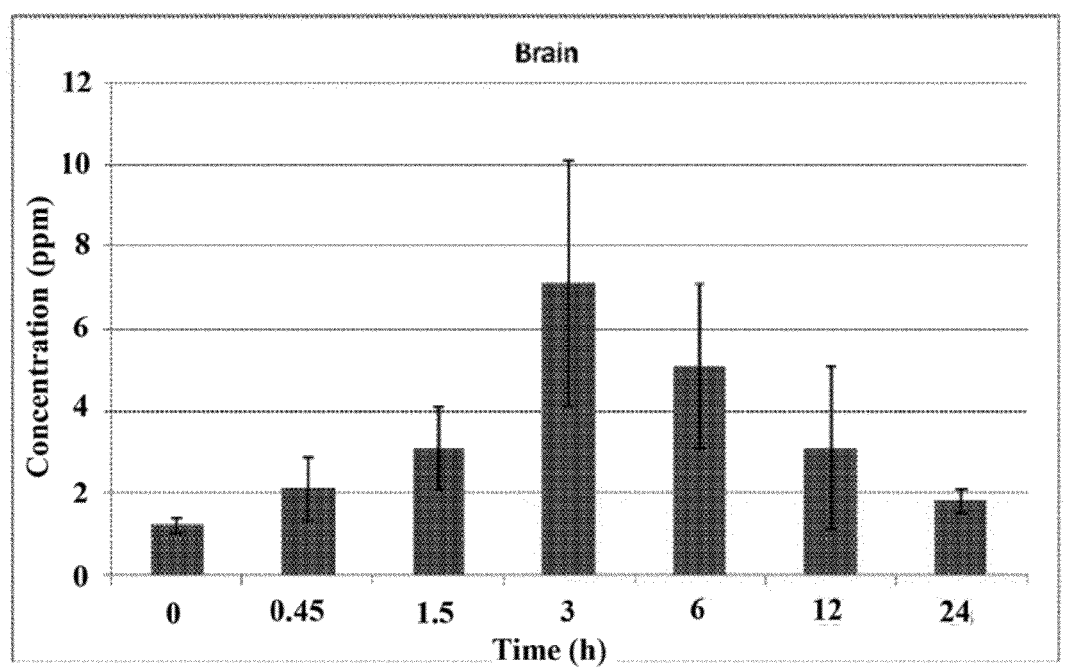
FIG. 17D shows a graphical representation of the biodistribution of the 10B-Drug in the brain of the body of the animal model in different times after injection (as per injection of 41.1 mg of enriched 10-Boron complex per every 30 gram of the animal's weight), according to one embodiment herein.
Figure 17E:
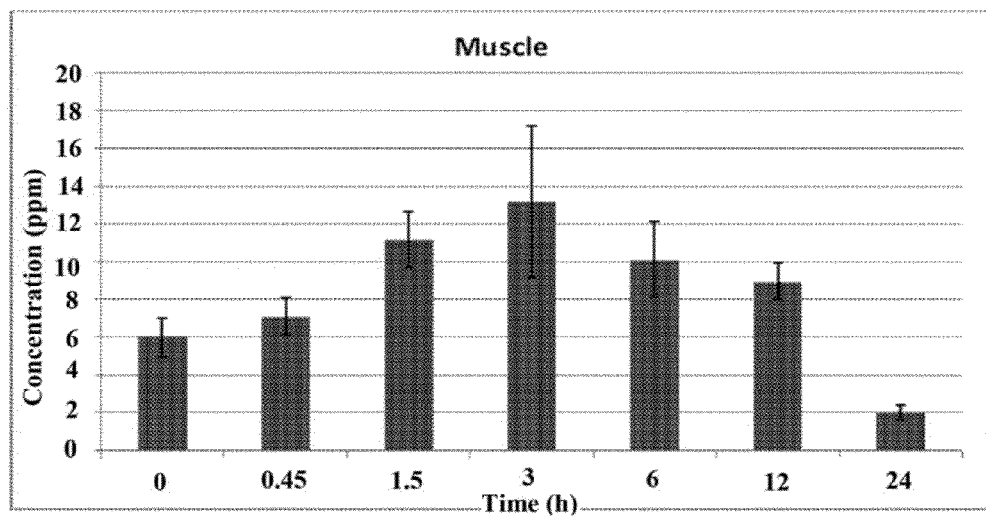
FIG. 17E shows a graphical representation of the biodistribution of the 10B-Drug in the muscle of the body of the animal model in different times after injection (as per injection of 41.1 mg of enriched 10-Boron complex per every 30 gram of the animal's weight), according to one embodiment herein.
Figure 17F:
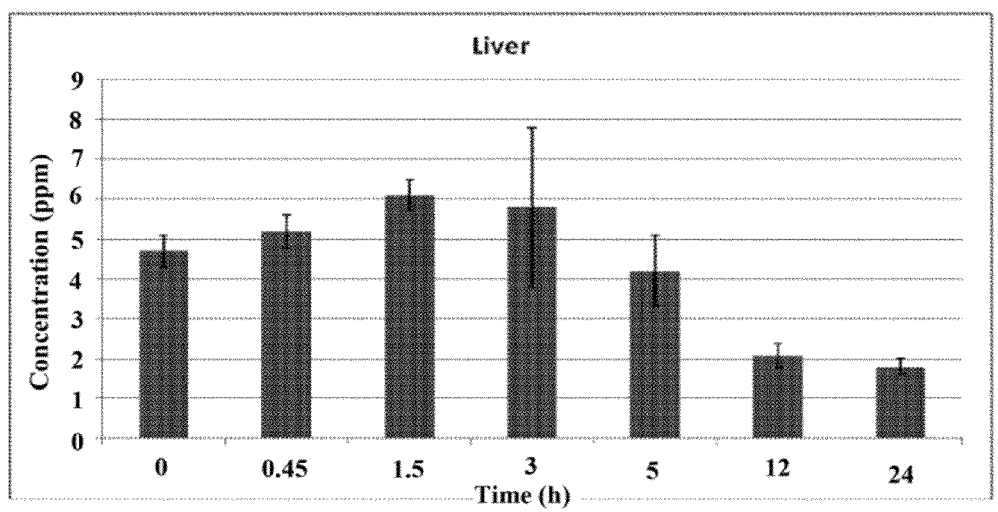
FIG. 17F shows a graphical representation of the bio distribution of the 10B-Drug in the liver of the body of the animal model in different times after injection (as per injection of 41.1 mg of enriched 10-Boron complex per every 30 gram of the animal's weight), according to one embodiment herein.
Figure 17G:
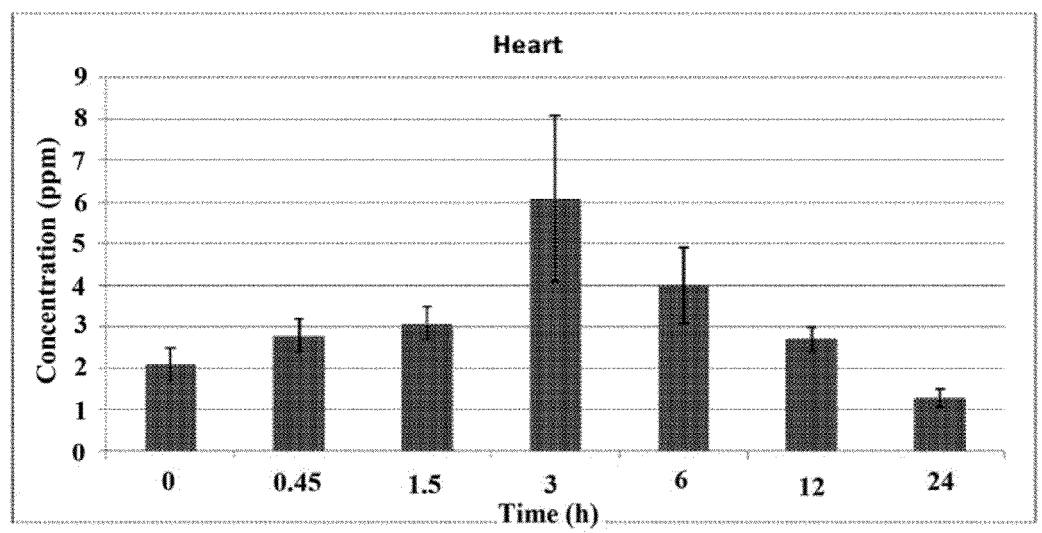
FIG. 17G shows a graphical representation of the bio distribution of the 10B-Drug in the heart of the body of the animal model in different times after injection (as per injection of 41.1 mg of enriched 10-Boron complex per every 30 gram of the animal's weight), according to one embodiment herein.
Figure 17H:
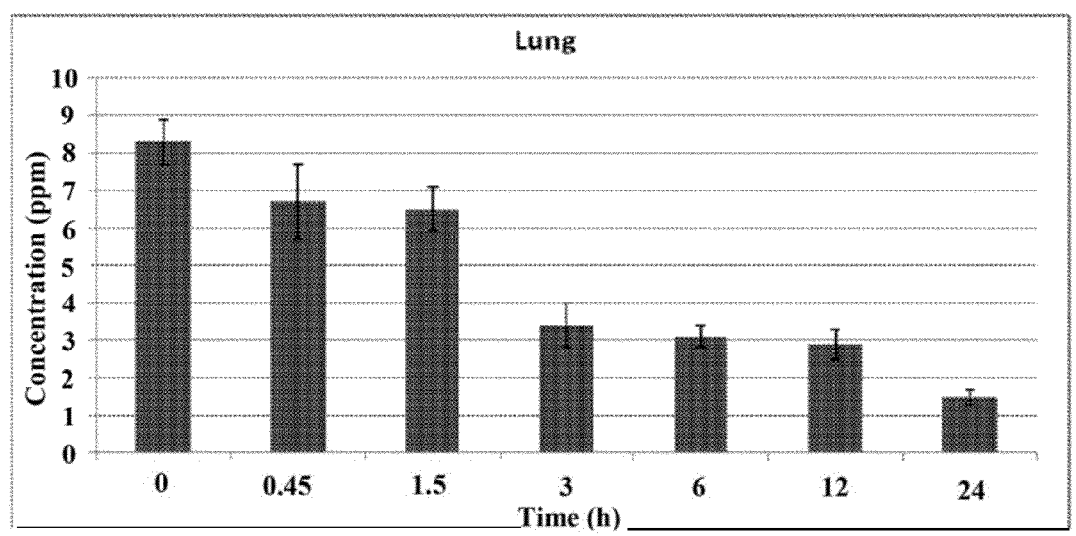
FIG. 17H shows a graphical representation of the bio distribution of the 10B-Drug in the lung of the body of the animal model in different times after injection (as per injection of 41.1 mg of enriched 10-Boron complex per every 30 gram of the animal's weight), according to one embodiment herein.
Figure 17I:
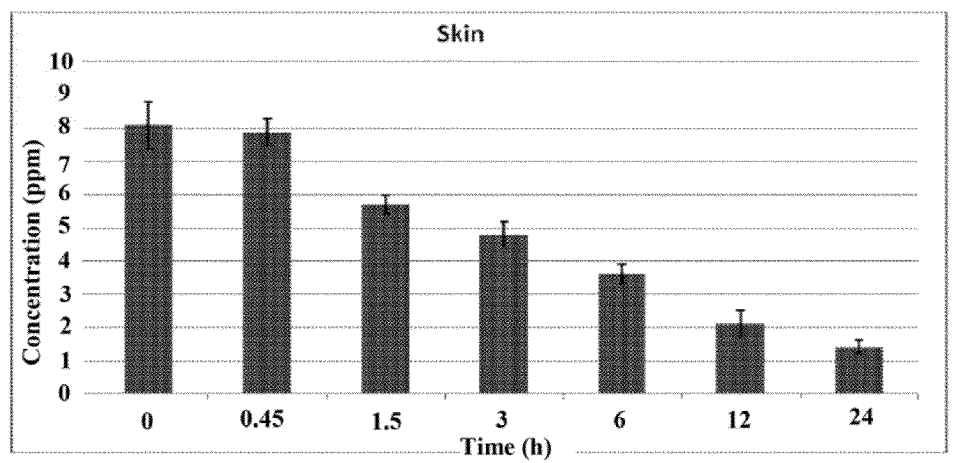
FIG. 17I shows a graphical representation of the bio distribution of the 10B-Drug in the skin of the body of the animal model in different times after injection (as per injection of 41.1 mg of enriched 10-Boron complex per every 30 gram of the animal's weight), according to one embodiment herein.
Figure 17J:
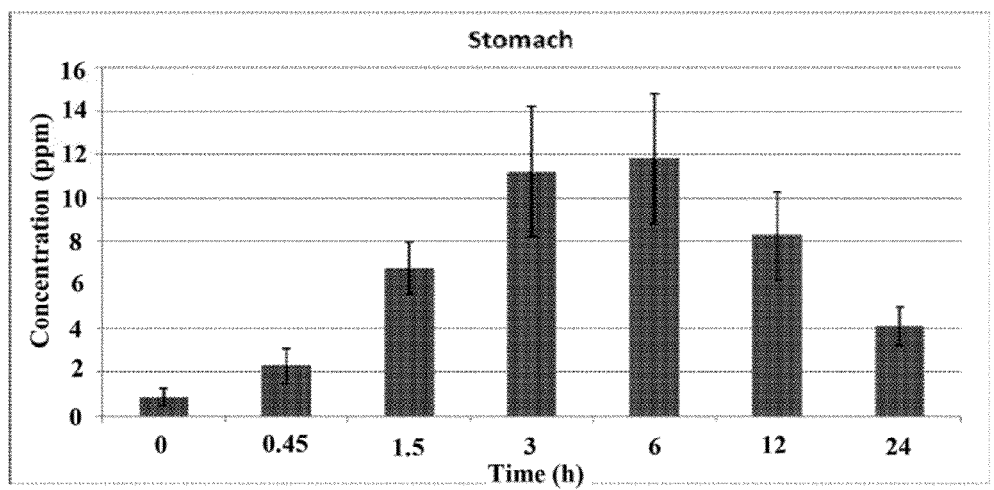
FIG. 17J shows a graphical representation of the bio distribution of the 10B-Drug in the stomach of the body of the animal model in different times after injection (as per injection of 41.1 mg of enriched 10-Boron complex per every 30 gram of the animal's weight), according to one embodiment herein.
Figure 17K:
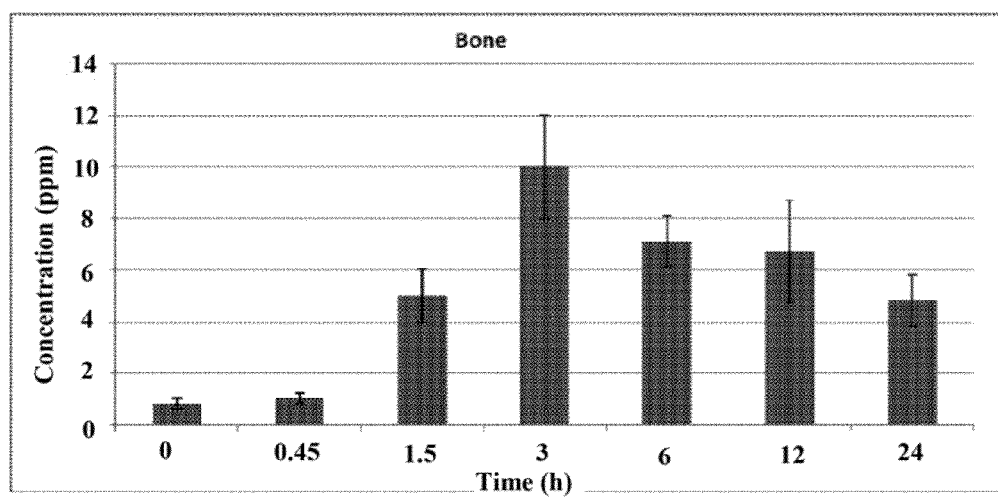
FIG. 17K shows a graphical representation of the bio distribution of the 10B-Drug in the bone of the body of the animal model in different times after injection (as per injection of 41.1 mg of enriched 10-Boron complex per every 30 gram of the animal's weight), according to one embodiment herein.

FIG. 16 shows a graphical representation of the toxicity of the synthesized composition using MTT assay method. With respect to FIG. 16, it can be observed that the fraction of living primary cells would not change significantly. This is due to the fact that since food composition was used in the synthesis of the drug, tumor cells think that they are provided with food compostions. But after a while the number of cells will decrease by the drug. For different concentrations of Boron including 5 mg, 10 mg, 25 mg, 50 mg and 100 mg, these decreases are equal to 80, 50, 64, 79, and 36. After 48 hours similar results with little differences have been observed with 24 hours time interval.

Dealing with the Accumulation of Enriched 10-Boron in Malignant Tissues and Tumors of Breast in In Vitro Medium with ICP Technique:

This is an empirical research which was carried out on 7 series of mice with the race of BULB/c (provided with Iran Pasteur research institute) at the age of 6 weeks which were kept in 22-25 centigrade degree and 50% humidity with 12 hours of light-dark cycle. A Tumor mouse with Spontaneous breast cancer was used as the stock tumor and tumor was egressed when the mouse was spinalized from its body in sterile situation, and then was divided into small pieces with surgical blade in sterile saline with scalpel, then each of the mice was anesthetized through injecting ketamin-zaylyn intra peritoneally (with dose of 10 mg/kg), and divided pieces of the tumor were transplanted under the skin to the right flank area through surgery. Then the location of surgery was stitched. Two weeks after transplantation, the growth of tumors was visible to the eye. For implementing the experiments, the study was divided into seven time groups: (a) zero, (b) 45 minutes, (c) 1 hour and a half, (d) 3 hours, (e) 6 hours, (f) 12 hours and finally (g) 12 hours. Then 41.1 mg of enriched 10-Boron complex was injected into peritoneal per 30 gram of the animal's weight. Then in a definite timing of 0, 45 minutes, 1.5 hour, 3 hours, 12 hours and 24 hours the animal was killed and all its tissues including tumor tissue, bone, kidney, brain, liver, heart, skin, stomach, blood, lung, spleen and muscles were studied in terms of the accumulation of the intended substance. In a way that the animal is killed in the mentioned times and the intended tissues have been separated and then were weighted through a precise scale. 50 mg of the tissue was immediately chosen for implementing following stages of ICP.

For lysis tissues 200 microliter of the intended digestion mixture containing 1/1 ratio of nitric acid and sulfuric acid was added to eppendorfs including containing tissues in 24 hours in the room temperature so the digestion will be carried out properly. After 24 hours, 600 microliter of Triton X-100 is added to the previous mixture. Then it was filtered out with 0.2 microliter filter and then its volume was reached to 2 ml and was kept in −20 centigrade degree. Then the experiment was repeated for 2 to 3 times for each sample of the accumulated amount of the intended substance in the mentioned tissues. The obtained results have been illustrated in FIG. 17A-17K. FIG. 17A-17K shows a Biodistribution of the synthesized drug according to the embodiments herein in the some component after various times after injection.

FIG. 17 A-FIG. 17 K shows a graphical representation of the distribution of the drug in the body of the patient in different times after injection, according to an embodiment herein. With respect to FIG. 17C, the studies illustrate that accumulation of 10-Boron in tumor cells is about 27 ppm which was a proper dose of neutron therapy (as per injection of 41.1 mg of enriched 10-Boron complex per every 30 gram of the animal's weight). On the other hand the figure illustrates that the provided drug will be connected to the cancerous cells purposefully and exclusively. This accumulation has been done 3 hours after injecting the drug. At the same time concentration of 10-Boron was about 6.1 ppm in the blood (as per injection of 41.1 mg of enriched 10-Boron complex per every 30 gram of the animal's weight), where concentration ratio of tumor to the 10-Boron concentration in the blood is about 4.5. This ratio is appropriate for 10-Boron neutron capture therapy.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A novel drug containing enriched 10-Boron for cancer cell treatment in Boron Neutron Capture Therapy (BNCT) comprising an Enriched 10-Boron Calcium Fructo Borate (E$^{10}$BCFB) having a Formula A or a Formula B, wherein the Formula A is represented by:

A

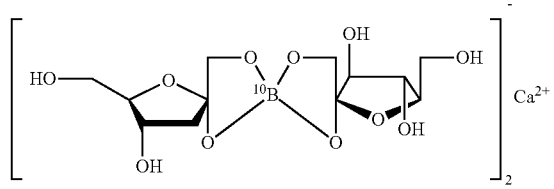

and wherein the Formula B is represented by:

B

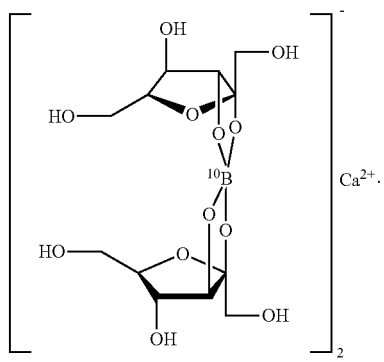

2. A method of synthesizing an enriched 10-Boron complex for Boron Neutron Capture Therapy (BNCT) comprising:
 dissolving a monosaccharide in a solvent at room temperature while stirring, wherein the solvent is water or alcohol, and wherein the monosaccharide is selected from a group consisting of a glucose and a fructose;
 adding a solution of an enriched $^{10}$B boric acid with maximum content of $^{10}$B to form a mixture;
 adjusting a pH of the mixture, wherein the pH of the mixture is adjusted to be equal to 3-4;
 adding a solution of a carbonate salt of calcium to the mixture while continuously stirring, wherein the solution of the carbonate salt of calcium is added after a produced carbon dioxide gas is completely removed from the mixture;
 forming a bi-phase solution, wherein the bi-phase solution comprises a lower phase and an upper phase, wherein the lower phase is a boron complex and wherein the upper phase is an oily liquid;
 separating the lower phase by scratching the lower phase using a glass bar;
 collecting the lower phase; and
 grinding the lower phase to obtain an enriched 10-Boron complex or a composition.

3. The method according to claim 2, wherein the enriched 10-Boron complex is Enriched 10-Boron Calcium Fructo Borate (E$^{10}$BCFB).

4. The method according to claim 2, wherein the enriched 10-Boron complex has a Formula A or a Formula B, and wherein the Formula A is represented by:

A

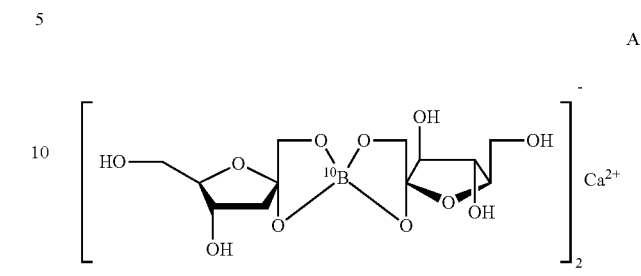

and wherein the Formula B is represented by:

B

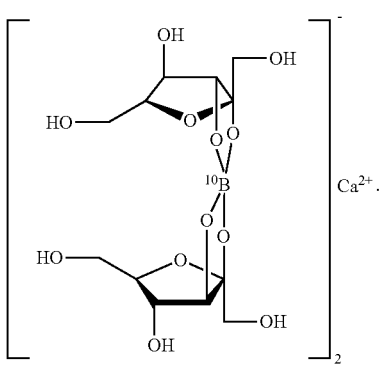

5. The method according to claim 2, wherein the monosaccharide is dissolved in the solvent at a concentration of 1 molar.

6. The method according to claim 2, wherein the solution of the enriched $^{10}$B boric acid has a concentration of 0.5-1 molar.

7. A method of treating cancer using Boron Neutron Capture Therapy (BNCT) comprising steps of:
 administering a drug composition containing the drug at a predetermined concentration to a patient, wherein the drug is Enriched 10-Boron Calcium Fructo Borate (E$^{10}$BCFB);
 allowing the accumulation of the drug in the tumor cells; and
 bombarding the tumor cells from outside the body using thermal or epithermal neutron beams;
 wherein the tumor cells are destroyed when the thermal or epithermal neutron beams come in to contact with the E$^{10}$BCFB.

8. The method according to claim 7, wherein the drug composition is administered orally and parenterally.

9. The method according to claim 7, wherein the predetermined concentration is 20 mcg $^{10}$B/g tumor to 35 mcg $^{10}$B/g tumor.

* * * * *